(12) United States Patent
Gehman et al.

(10) Patent No.: US 8,168,433 B2
(45) Date of Patent: May 1, 2012

(54) CELL CULTURE ARTICLE AND SCREENING

(75) Inventors: Jennifer Gehman, Painted Post, NY (US); Arthur W. Martin, Horseheads, NY (US); Zara Melkoumian, Painted Post, NY (US); Christopher B. Shogbon, Corning, NY (US); David M. Weber, Corning, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 664 days.

(21) Appl. No.: 12/362,782

(22) Filed: Jan. 30, 2009

(65) Prior Publication Data
US 2009/0203065 A1    Aug. 13, 2009

Related U.S. Application Data

(60) Provisional application No. 61/062,890, filed on Jan. 30, 2008, provisional application No. 61/062,937, filed on Jan. 30, 2008.

(51) Int. Cl.
*C12N 5/00*      (2006.01)
*C12N 11/08*     (2006.01)
*C08F 120/18*    (2006.01)
*C07K 17/08*     (2006.01)
*C07K 17/06*     (2006.01)

(52) U.S. Cl. ............. 435/402; 435/180; 526/329.7; 530/402

(58) Field of Classification Search ............. 435/402, 435/180; 526/329.7; 530/402
See application file for complete search history.

(56) References Cited

U.S. PATENT DOCUMENTS

| | | | |
|---|---|---|---|
| 4,578,079 A | 3/1986 | Ruoslahti et al. | 523/11 |
| 4,792,525 A | 12/1988 | Ruoslahti et al. | 435/240.243 |
| 4,908,236 A | 3/1990 | Pitt et al. | 427/245 |
| 5,278,063 A | 1/1994 | Hubbell et al. | 435/240.243 |
| 5,330,911 A | 7/1994 | Hubbell et al. | 435/240.243 |
| 5,480,953 A | 1/1996 | Sugaya et al. | 526/320 |
| 5,643,561 A | 7/1997 | Katsuen et al. | 424/78.17 |
| 5,691,203 A | 11/1997 | Katsuen et al. | 435/402 |
| 5,695,997 A | 12/1997 | Ruoslahti et al. | 435/375 |
| 5,916,875 A | 6/1999 | Ruoslahti et al. | 514/12 |
| 6,121,027 A | 9/2000 | Clapper et al. | 435/180 |
| 6,306,922 B1 | 10/2001 | Hubbell et al. | 522/71 |

(Continued)

FOREIGN PATENT DOCUMENTS

EP       0614923 B1     1/2000

(Continued)

OTHER PUBLICATIONS

Anderson, Daniel G., Levenberg, Shulamit, Langer, Robert, Nanoliter-scale synthesis of arrayed biomaterials and application to human embryonic stem cells, Nature Biotechnology vol. 22, No. 7, Jul. 2004, 863-866.

(Continued)

*Primary Examiner* — Rosanne Kosson
(74) *Attorney, Agent, or Firm* — Susan S. Wilks

(57) ABSTRACT

A method for producing a cell culture article having a synthetic polymer layer for incubating with cells includes diluting one or more (meth)acrylate monomers in a solvent and dispersing the diluted monomers on a surface of the cell culture article. Some or substantially all of the solvent is removed and the monomers are then polymerized on the surface of the article to form the synthetic polymer layer attached to the surface of the article.

19 Claims, 16 Drawing Sheets

U.S. PATENT DOCUMENTS

| | | | |
|---|---|---|---|
| 6,316,522 B1 | 11/2001 | Loomis et al. | 523/105 |
| 6,514,734 B1 | 2/2003 | Clapper et al. | 435/180 |
| 6,534,130 B1 | 3/2003 | Maag et al. | 427/492 |
| 6,897,271 B1 | 5/2005 | Domschke et al. | 526/91 |
| 7,067,194 B2 | 6/2006 | Mao et al. | 428/429 |
| 7,384,984 B2 | 6/2008 | Lewandowski et al. | 514/772.1 |
| 7,402,339 B2 | 7/2008 | Schmidt et al. | 428/407 |
| 2003/0029418 A1 | 2/2003 | Deschamps et al. | 123/376 |
| 2003/0083389 A1 | 5/2003 | Kao et al. | 516/98 |
| 2003/0215946 A1 | 11/2003 | Nair et al. | 435/395 |
| 2005/0019747 A1 | 1/2005 | Anderson et al. | 435/4 |
| 2005/0036980 A1 | 2/2005 | Chaney et al. | 424/78.27 |
| 2005/0059150 A1 | 3/2005 | Guarino et al. | 435/370 |
| 2005/0136536 A1 | 6/2005 | Anderson et al. | 435/366 |
| 2005/0265980 A1 | 12/2005 | Chen et al. | 424/93.7 |
| 2005/0276858 A1 | 12/2005 | Kao et al. | 424/487 |
| 2005/0281857 A1 | 12/2005 | Heyer et al. | 424/423 |
| 2006/0100369 A1 | 5/2006 | Kao et al. | 525/54.1 |
| 2006/0127878 A1 | 6/2006 | Salomon et al. | 435/4 |
| 2006/0134050 A1 | 6/2006 | Griffith et al. | 424/70.16 |
| 2006/0263878 A1 | 11/2006 | Mochitate | 435/366 |
| 2007/0026518 A1 | 2/2007 | Healy et al. | 435/325 |
| 2007/0029924 A1 | 2/2007 | Ushifusa et al. | 313/496 |
| 2007/0167354 A1 | 7/2007 | Kennedy et al. | 514/8 |
| 2007/0269886 A1 | 11/2007 | Qian et al. | 435/366 |
| 2009/0043079 A1 | 2/2009 | Chen et al. | 530/402 |
| 2010/0099160 A1* | 4/2010 | Jiang et al. | 435/180 |

FOREIGN PATENT DOCUMENTS

| | | |
|---|---|---|
| JP | 58-146280 | 8/1983 |
| JP | 01-309682 | 12/1989 |
| JP | 2002-191353 | 7/2002 |
| JP | 2006-042794 | 2/2006 |
| JP | 2006-174826 | 7/2006 |
| WO | 98/31734 | 7/1998 |
| WO | 02/06373 A1 | 1/2002 |
| WO | 02/062961 A2 | 8/2002 |
| WO | 02/062969 A2 | 8/2002 |
| WO | 03/029418 A2 | 4/2003 |
| WO | 2004/037164 A2 | 5/2004 |
| WO | 2005/028619 | 3/2005 |
| WO | 2006/105278 A2 | 10/2006 |
| WO | 2007/012144 | 2/2007 |
| WO | 2007/104107 A1 | 9/2007 |
| WO | 2008/118392 A2 | 10/2008 |

OTHER PUBLICATIONS

Barber, T.A., Harbers, G.M., Park, S., Gilbert, M., Healy, K.E., "Ligand Density Characterization of Peptide-Modified Biomaterials," Biomaterials, 26(34), 6897-6905 (2005).

Barber, T.A., Golledge, S.L., Castner, D.G, and Healy, K.E., "Peptide-modified p(AAm-co-EG/AAc) IPNS Grafted to Bulk Titanium Modulate Osteoblast Behavior In Vitro," J. Biomed. Mater. Res., 64A, 38-47 (2003).

Bearinger, J.P., Castner, D.G., and Healy, K.E., "Biomolecular Modification of P(AAm-co-EG/AA) IPNs Supports Osteoblast Adhesion and Phenotypic Expression," J. Biomaterials Science:Polymer Ed., 9(7), 629-652 (1998).

Bearinger, J.P., Castner, D.G., Chen, J., Hubchak, S., Golledge, S.L., and Healy, K.E., "P(AAm-co-EG) Interpenetrating Polymer Networks Grafted to Oxide Surfaces: Surface Characterization, Protein Adsorption, and Cell Detachment Studies," Langmuir, 13(19), 5175-5183 (1997).

Braam, Stefan R, et al., Recombinant Vitronectin Is a Functionally Defined Substrate that Supports Human Embryonic Stem Cell Self Renewal Via AVB5 Integrin, Stem Cells express, Jul. 3, 2008, 1-20.

Brandley, B.K., et al., "Covalent Attachment of an Arg-Gyl-Asp Sequence Peptide to Derivatizable Polyacrylamide Surfaces: Sequence Peptide to Derivatizable Polyacrylamide Surfaces: Support of Fibroblast Adhesion and Long-Term Growth", Analytical Biochemistry, vol. 172, 1988, 270-278.

Drumheller PD, Herbert CB, Hubbell JA; "Bioactive Peptides and Surface Design", Interfacial Phenomena and Bioproducts, J.L. Brash et al., Marcel Dekker, Inc, 1996, pp. 273-310.

Cruise GM, Scharp DS, and Hubbell JA. Characterization of permeability and network structure of interfacially photopolymerized poly-(ethylene glycol) diacrylate hydrogels. Biomaterials 19: 1287-1294, 1998.

Dawson, Eileen, et al., "Biomaterials for stem cell differentiation", Advanced Drug Delivery Reviews, vol. 60, 2008, 215-228.

Drumheller, Paul D., Elbert, Donald L., Hubbell, Jeffrey A., Multifunctional Poly(ethylene glycol) Semi-Interpenetrating Polymer Networks as Highly Selective Adhesive Substrates for Bioadhesive Peptide Grafting, Biotechnology and Bioengineering, vol. 43, pp. 772-780, (1994).

Drumheller PD and Hubbell JA. Polymer networks with grafted cell adhesion peptides for highly biospecific cell adhesive substrates. Anal Biochem 222: 380-388, 1994.

Drumheller P.D. and Hubbell J.A.: Surface immobilization of adhesion ligands for investigations of cell/substrate interactions. In: The Biomedical Engineering Handbook, J.D. Bronzino Ed., CRC and IEEE Press 1583-1596, 1995.

Fittkau MH, Zilla P, Bezuidenhout D, Lutolf MP, Human P, Hubbell JA, and Davies N. The selective modulation of endothelial cell mobility on RGD peptide containing surfaces by YIGSR peptides. Biomaterials 26: 167-174, 2005.

Harbers G.M., Gamble L.J., Irwin E.F., Cashier D.G., Healy K.E., "Development and Characterization of a High-Throughput System for Assessing Cell-Surface Receptor-Ligand Engagement," Langmuir, 21(18), 8374-84 (2005).

Harbers G.M., Healy, K.E., "The Effect of Ligand Type and Density on Osteoblast Adhesion, Proliferation, and Matrix Mineralization," J. Biomed. Mater. Res. Part A, 75A, 855-869 (2005).

Healy, K.E., Rezania, A., and Stile, A., "Designing Biomaterials to Direct Biological Responses," Annals of the New York Academy of Sciences, 875, 24-35 (1999).

Healy, K.E., "Molecular Engineering of Materials for Bioreactivity," Current Opinion in Solid State and Materials Science, 4, 381-387 (1999).

Heggli M, Tirelli N, Zisch A, and Hubbell JA. Michael-type addition as a tool for surface functionalization. Bioconjug Chem 14: 967-973, 2003.

Hern DL and Hubbell JA. Incorporation of adhesion peptides into nonadhesive hydrogels useful for tissue resurfacing. J Biomed Mater Res 39: 266-276, 1998.

Hubbell JA. Biomaterials in tissue engineering. Biotechnology (NY) 13: 565-576, 1995.

Hubbell JA, Massia SP, and Drumheller PD. Surface-grafted cell-binding peptides in tissue engineering of the vascular graft. Ann NY Acad Sci 665: 253-258, 1992.

Huebsch, N., Gilbert, M., Healy, KE., "Analysis of Sterilization Protocols for Peptide-Modified Hydrogels," J. Biomed. Mater. Res. Part B, 74B(1), 440-447 (2005).

Irwin, E.F., Ho, J.E., Kane, S.R., Healy, K.E., "Analysis of Interpenetrating Polymer Networks via Quartz Crystal Microbalance with Dissipation Monitoring," Langmuir, 21(12), 5529-5536 (2005).

Kim, S.-Y., Chung, E., Gilbert, M., and Healy, K.E., "Synthetic MMP-13 Degradable ECMs Based on Poly(N-isopropyl acrylamide-co-Acrylic acid) Semi-Interpenetrating Polymer Networks I. Degradation and Cell Migration," J. Biomed. Mater. Res. Part A, 75(1), 73-88 (2005).

Kim, S.-Y., and Healy, K.E., "Synthesis and Characterization of Injectable Poly(N-isopropylacrylamide-co-Acrylic acid) Hydrogels with Proteolytically Degradable Cross-links," Biomacromolecules, 4, 1214-1223 (2003).

Li Y, Powell S, Brunette E, Lebkowski J, Mandalam R. Expansion of human embryonic stem cells in defined serum-free medium devoid of animal-derived products. Biotechnol Bioeng. 91(6):688-98, 2005.

Li, Y.J., Chung, E.H., Rodriguez, R.T., Firpo, M.T., Healy, K.E., "Hydrogels as Artificial Matrices for Human Embryonic Stem Cell Self-Renewal," J. Biomed. Mater. Res. Part A, 79(1), 1-5 (2006).

Lu J, Hou R, Booth C, Yang S, Snyder M. Defined culture conditions of human embryonic stem cells. PNAS USA. 103(15):5688-93, 2006.

Ludwig TE, Levenstein ME, Jones JM, Berggren WT, Mitchen ER, Frane JL, Crandall LJ, Daigh CA, Conard KR, Piekarczyk MS, Llanas RA, Thomson JA. Derivation of human embryonic stem cells in defined conditions. Nat Biotechnol. 24(2):185-7, 2006.

Lutolf MP and Hubbell JA. Synthetic biomaterials as instructive extracellular microenvironments for morphogenesis in tissue engineering. Nat Biotechnol 23: 47-55, 2005.

Lutolf MP and Hubbell JA. Synthesis and physicochemical characterization of end-linked poly(ethylene glycol)-co-peptide hydrogels formed by Michael-type addition. Biomacromolecules 4: 713-722, 2003.

Massia SP and Hubbell JA. An RGD spacing of 440 nm is sufficient for integrin alpha V beta 3-mediated fibroblast spreading and 140 nm for focal contact and stress fiber formation. J Cell Biol 114: 1089-1100, 1991.

Massia SP, Rao SS, and Hubbell JA. Covalently immobilized laminin peptide Tyr-Ile-Gly-Ser-Arg (YIGSR) supports cell spreading and co-localization of the 67-kilodalton laminin receptor with alpha-actinin and vinculin. J Biol Chem 268: 8053-8059, 1993.

Massia SP and Hubbell JA. Human endothelial cell interactions with surface-coupled adhesion peptides on a nonadhesive glass substrate and two polymeric biomaterials. J Biomed Mater Res 25: 223-242, 1991.

Massia SP and Hubbell JA. Immobilized amines and basic amino acids as mimetic heparin-binding domains for cell surface proteoglycan-mediated adhesion. J Biol Chem 267: 10133-10141, 1992.

Massia SP and Hubbell JA. Vascular endothelial cell adhesion and spreading promoted by the peptide REDV of the IIICS region of plasma fibronectin is mediated by integrin alpha 4 beta 1. J Biol Chem 267: 14019-14026, 1992.

Model, M., and Healy, K.E., "Quantification of the Surface Density of a Fluorescent Label with the Optical Microscope," J. Biomed. Mater. Res., 50, 90-96 (2000).

Park, S., and Healy, K.E., "Nanoparticulate DNA Packaging Using Terpolymers of Poly(lysine-g-lactide-b-ethylene glycol)," Bioconjugate Chemistry, 14(2), 311-319 (2003).

Park, S., Bearinger, J.P., Lautenschlager, E.P., Castner, D.G., Healy, K.E., "Surface Modification of Poly(ethylene terephthalate) Anigoplasty Balloons with a Hydrophilic Poly(acrylamide-co-ethylene glycol) Interpenetrating Network Coating," J. Biomed. Mater. Res., 53(5), 568-576 (2000).

Pratt, A.B., et al., Synthetic Extracellular Matrices for In Situ Tissue Engineering, Biotechnology and Bioengineering, vol. 86, No. 1, Apr. 5, 2004, 27-36.

Rezania, A., Thomas, C.H., and Healy, K.E., "A Probabilistic Approach to Measure the Strength of Bone Cell Adhesion to Chemically Modified Surfaces," Annals of Biomedical Engineering, 25, 190-203 (1997).

Rezania, A., Johnson, B., Lefkow, AR, and Healy, K.E., "Bioactivation of Metal Oxide Surfaces: I. Surface Characterization and Cell Response," Langmuir, 15, 6931-6939 (1999).

Rezania, A., and Healy, K.E., "Biomimetic Peptide Surfaces that Regulate Adhesion, Spreading, Cytoskeletal Organization, and Mineralization of the Matrix Deposited by Osteoblast-like Cells," Biotechnology Progress, 15(1), 19-32 (1999).

Rezania, A., and Healy, K.E., "Biomolecular Surface Engineering of Materials for Controlling Bone Cell Adhesion and Spreading," Mat. Res. Soc. Symp. Proc., 530, 99-103 (1998).

Rezania, A., and Healy, K.E., "Integrins Subunits Responsible for Adhesion of Human Osteoblast-Like Cells to Biomimetic Peptide Surfaces," J. Ortho. Res., 17(4), 615-623 (1999).

Rezania, A., Thomas, C.H., and Healy, K.E., "The Detachment Strength and Morphology of Bone Cells Contacting Materials Modified with a Peptide Sequence Found within Bone Sialoprotein," J. Biomedical Materials Res., 37(1), 9-19 (1997).

Rezania, A., and Healy, K.E., "The Effect of Peptide Surface Density on Mineralization of a Matrix Deposited by Osteogenic Cells," J.Biomed. Mater. Res., 52, 595-600 (2000).

Saha et al., Journal of Biomedical Materials Research Part A, Biomimetric interfacial interpenetration polymer networks control neural stem cell behavior, (2007), 81(1):240-249.

Skottman H and Hovatta O. Culture conditions for human embryonic stem cells. Reproduction. 132(5):691-8, 2006.

Stile, R. A., Shull, K.R., and Healy, K. E., "Axisymetric Adhesion Test to Examine the Interfacial Interactions between Biologically-Modified Networks and Models of the Extracellular Matrix," Langmuir, 19, 1853-1860 (2003).

Stile RA., Chung E., Burghardt, W.R., Healy, K.E., "Poly(N-isopropylactylamide)-based Semi-Interpenetrating Polymer Networks for Tissue Engineering Applications. Effects of Linear Poly(acrylic acid) Chains on Rheology," J. Biomater. Sci. Polym. Ed., 15(7), 865-878 (2004).

Stile, R.A., and Healy, K.E., "Poly(N-isopropylacrylamide)-based Semi-Interpenetrating Polymer Networks for Tissue Engineering Applications Effects of Linear Poly(acrylic acid) Chains on Phase Behavior," Biomacromolecules, 3, 591-600 (2002).

Stile, R.A., Burghardt, W.R., and Healy, K.E., "Synthesis and Characterization of Injectable Poly(N-isopropylacrylamide)-based Hydrogels that Support Tissue Formation In Vitro," Macromolecules, 32, 7370-7379 (1999).

Stile, R.A., and Healy, K.E., "Thermo-Responsive Peptide-Modified Hydrogels for Tissue Regeneration," Biomacromolecules, 2, 185-194 (2001).

Stojkovic P. Lako M. Przvborski S. Stewart R., Armstrong L. Evans J. Zhang X. Stojkovic M. Human-serum matrix supports undifferentiated growth of human embryonic stem cells. Stem Cells. 23(7):895-902, 2005.

Thomas, C.H., L'Hoest, J-B., Castner, D.G., McFarland, C.D., and Healy, K.E., "Materials Designed to Control and Examine the Function of Single Cells," Mat. Res. Soc. Symp. Proc., 530, 55-58 (1998).

Whang, K., Goldstick, T.K., Healy, K.E., "A Biodegradable Polymer Scaffold for Delivery of Osteotropic Factors," Biomaterials, 21, 2545-2551 (2000).

* cited by examiner

A)

SEQUENCE LISTING

```
<160> NUMBER OF SEQ ID NOS: 1

<210> SEQ ID NO 1
<211> LENGTH: 15
<212> TYPE: PRT
<213> ORGANISM: mouse

<400> SEQUENCE: 1

Lys Gly Gly Asn Gly Glu Pro Arg Gly Asp Thr Tyr Arg Ala Tyr
1               5                   10                  15
```

CELL CULTURE ARTICLE AND SCREENING

RELATED APPLICATION(S)

This application claims the benefit of U.S. Provisional Application Ser. No. 61/062,890 filed Jan. 30, 2008 and entitled "Synthetic Surfaces for Culturing Undifferentiated Stem Cells in Chemically Defined Media" and U.S. Provisional Application Ser. No. 61/062,937 filed Jan. 30, 2008 and entitled "Stem Cell Article and Screening."

FIELD

The present disclosure relates to cell culture articles and methods for producing surfaces thereon, and more particularly for producing surfaces for cell culture including stem cell attachment and growth.

BACKGROUND

Pluripotent stem cells such as human embryonic stem cells (hESCs) have the ability to differentiate into any of the three germ layers, giving rise to any adult cell type in the human body. This unique property provides a potential for developing new treatments for a number of serious cell degenerative diseases, such as diabetes, spinal chord injury, heart diseases and the like. In addition, cells derived from hESCs can be used for drug discovery and toxicology studies. Several groups have already demonstrated the differentiation of hESCs into different cell types. However, major obstacles in the development of such hESC-based treatments include (i) obtaining and maintaining adequate numbers of undifferentiated hESCs in cell and tissue culture and (ii) controlling their differentiation in order to produce specific cell types. Stem cell cultures, such as hESC cell cultures are typically seeded with a small number of cells from a cell bank or stock and then amplified in the undifferentiated state until differentiation is desired for a given therapeutic application. One current way to accomplish this is to culture the hESCs or their differentiated cells in the presence of surfaces and media containing animal-derived components, such as feeder layers, fetal bovine serum, or MATRIGEL™ available from BD Biosciences San Jose, Calif. These additions to the culture environment expose the cells to potentially harmful viruses or other infectious agents which could be transferred to patients or compromise general culture and maintenance of undifferentiated hESC. In addition, those biological culture products are also vulnerable to batch variation, immune response and limited shelf-life.

Synthetic surfaces have the potential to provide significant benefits to prevent the above concerns. However, the effects of synthetic surfaces on the behavior of stem cells, in particular, hESCs, have not been studied in great detail. Nanoliter-scale synthesis of arrayed synthetic biomaterials has been proposed for performing high throughput screening for hESC culture application. However, such small scale culture presents several problems. For example, due to the size of each spot in the array, the number of cells in each spot is limited and the corresponding cell response is questionable.

Problems also exist with regard to employing such screening systems on a larger scale, such as with traditional cell culture glass-ware or plastic-ware. For example, obtaining uniform, non-toxic surfaces for reliable culturing and screening can be difficult, particularly with polymeric mixtures having a high viscosity. For example, the high viscosity can reduce the speed at which surfaces may be produced, and thus may be too inefficient for high throughput screening. Further high viscosity fluids can result in non-uniform coatings on a large surface area, thereby hindering the ability to reliably determine cell responses.

BRIEF SUMMARY

The present disclosure presents, inter alia, a coating process that (i) allows for high throughput screening of synthetic surfaces for stem cell culture and (ii) provides a uniform surface for reliably detecting cell responses to the synthetic surfaces. In addition, the present disclosure provides a coating process which provides a surface suitable for large scale cell culture.

In an embodiment, a method for producing a cell culture article having a synthetic polymer layer for incubating with cells is described. The method includes diluting one or more (meth)acrylate monomers in a solvent and dispersing the diluted monomers on a surface of the cell culture article. About 80% or more of the solvent is removed, e.g. by evaporation. The method further includes polymerizing the monomers on the surface of the article after removing the about 80% or more of the solvent to form the synthetic polymer layer attached to the surface of the article (in situ polymerization).

In an embodiment, a method for screening cell-synthetic polymer layer interactions is described. The method includes diluting, in a solvent, selected members of a library including members of one or more (meth)acrylate monomers and dispersing the diluted selected members into wells of one or more cell culture articles. The members are dispersed such that a given diluted selected member is dispersed in a given well. The method also includes removing about 80% or more of the solvent from the wells and then polymerizing the monomers of the selected members in the wells to form the synthetic polymer layers. The method also includes incubating the synthetic polymer layers in the wells with cells in a cell culture medium and characterizing a predetermined cell (e.g. stem cell) behavior for each synthetic polymer layer with which the cells are incubated.

One or more of the various embodiments presented herein provide one or more advantages over prior proposed methods for screening synthetic surfaces for their ability to support culturing of cells. For example, use of a solvent in the synthetic surface production process reduces monomer viscosity, allowing automated equipment to be used, saving time and labor. It also promotes monomer spreading to achieve a thin or more uniform coating, reducing monomer consumption and increasing the reliability of determinations as to whether the surface is suitable for supporting culture of selected cells. Further, use of a solvent tends to reduce the possibility of delamination of the coated surface from the substrate. Use of certain selected solvents, such as ethanol or 2-propanol, also provides several advantages, which may include low toxicity, compatibility with a large number of monomers and cell culture ware, compatibility with free radical polymerization, or the like. In addition, the use of in situ polymerization forms a polymeric network, which is not an interpenetrating network, which may provide a surface which is resistant to delamination and amenable to cell culture. These and other advantages will be readily understood from the following detailed descriptions when read in conjunction with the accompanying drawings

Figure 1A:
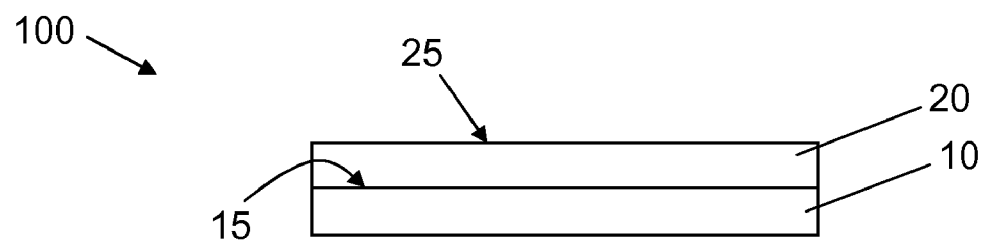
FIGS. 1A-C are schematic diagrams of side views of synthetic polymer layer coated articles.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "monomer" means a compound capable of polymerizing with another monomer, (regardless of whether the "monomer" is of the same or different compound than the other monomer), which compound has a molecular weight of less that about 1000 Dalton. In many cases, monomers will have a molecular weight of less than about 400 Dalton.

The term "hydrogel" has been used to describe cell culture surfaces. "Hydrogel" has been variously defined to include a gel or gelatin that can absorb water in an amount greater than or equal to 30% or up to 10,000% of its dry weight. When contacted with water, hydrogels swell but do not dissolve. The term "hydrogel" is a very broad term, describing a wide range of materials, having a wide range of water swelling and water absorbing characteristics.

As used herein, "swellable (meth)acrylate" or "SA" means a synthetic polymer layer made from at least one ethylenically unsaturated monomer (acrylate or methacrylate monomers) having at least some degree of cross linking, and also having water absorbing or water swelling characteristics. Swellable (meth)acrylates may be synthetic. That is, they do not contain ingredients that are derived from animals or animal extracts. Swellable (meth)acrylates may be conjugated to peptides or proteins ("swellable (meth)acrylate-peptide" or "SAP"). Peptides or proteins may be synthesized or obtained through recombinant techniques, making them synthetic, non-animal-derived materials. This SA and SAP material may be referred to as a layer, a coating, a surface, a material, or any other term known in the art to refer to a surface suitable for cell culture. The particular peptide sequence may be further identified. For example, a SAP surface may be conjugated with a BSP or vitronectin peptide sequence and may be identified as SAP-BSP or SAP-VN. In embodiments of the present disclosure, the term "swellable (meth)acrylate" represents a range of cross-linked acrylate or methacrylate materials which absorb water, swell in water, and do not dissolve in water. This water-absorbing characteristic can be described and measured by equilibrium water content (EWC) as shown by Formula 1:

$$EWC(\%)=(Wgel-Wdry)/(Wgel*100) \qquad \text{Formula 1}$$

The EWC of embodiments of swellable (meth)acrylates of the present disclosure range between 5% and 70% in water, and may be pH dependent. EWC can also be measured after exposure to other liquids such as buffer (for example, phosphate buffer, at pH 7.4). In various embodiments, the EWC (in water) of SAs of the present disclosure may range between 5% and 70%, between 5% and 50%, between 5% and 40%, between 10% and 40% between 5% and 35%, between 10% and 35% or between 15% and 35% in water. In some embodiments, after the swellable (meth)acrylates have been conjugated with peptides (SAP), the EWC of embodiments of SAPs of the present disclosure may be, for example, between 10-40% in water.

In cell culture, prepared surfaces are exposed to an aqueous environment for extended periods of time. Surfaces that absorb significant water, surfaces that are highly hydrogel-like, may tend to delaminate from a substrate when exposed to an aqueous environment. This may be especially true when these materials are exposed to an aqueous environment for extended periods of time, such as for 5 or more days of cell culture. Accordingly, it may be desirable for SA and SAP layers to have lower EWC measurements, and therefore do not absorb as much water, to reduce the likelihood of delaminating. For example, SA surfaces having an EWC below 40% may be particularly suitable for supporting hES cells in culture.

As used herein, "cyclic olefin copolymer" means a polymer formed from more than one monomer species, where at least one of the monomer species is a cyclic olefin monomer and at least one other monomer species is not a cyclic olefin monomer species. In many embodiments, cyclic olefin copolymers are formed from ethylene and norbonene monomers. Cyclic olefin copolymer resins are commercially available with trade name of TOPAS® from Boedeker Plastics, Inc.

Unless stated otherwise, ratios of compounds in a composition, such as a solution, are stated on a by volume basis.

As used herein, "have", "having", "include", "including", "comprise", "comprising" or the like are used in their open ended sense, and generally mean "including, but not limited to".

The present disclosure describes, inter alia, articles for culturing cells, methods for producing articles for cell culture and methods for screening surfaces for their ability to support cultured cells. Various embodiments presented herein provide for the ability to produce uniform, non-toxic synthetic polymer coatings for use in high throughput screening to identify synthetic coatings that provide favorable interactions with cultured cells.

1. Cell Culture Article

Referring to FIG. 1, a schematic diagram of article 100 for culturing cells is shown. The article 100 includes a cell culture substrate or base material substrate 10 having a surface 15. A synthetic polymer coating layer 20 is disposed on the surface 15 of the cell culture substrate or base material 10. While not shown, it will be understood that synthetic polymer coating 20 may be disposed on a portion of cell culture substrate or base material 10. The cell culture substrate or base material 10 may be any material suitable for culturing cells, including a ceramic substance, a glass, a plastic, a polymer or co-polymer, any combinations thereof, or a coating of one material on another. Such base materials 10 include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

Examples of articles 100 suitable for cell culture include single and multi-well plates, such as 6, 12, 96, 384, and 1536 well plates, jars, petri dishes, flasks, multi-layer flasks, Cell-Stack®, beakers, plates, roller bottles, slides, such as chambered and multichambered culture slides, tubes, cover slips, bags, membranes, hollow fiber, beads and microcarriers, cups, spinner bottles, perfusion chambers, bioreactors, and fermenters.

Synthetic polymer coating 20 provides a surface 25 on which cells may be cultured or screened. Synthetic polymer coating may be referred to as synthetic polymer layer, synthetic polymer coating, synthetic polymer surface or any other suitable term. In numerous embodiments, synthetic polymer surface 20 is formed of polymerized (meth)acrylate monomers. Of course synthetic polymer surface 20 may be formed from any other suitable class of biocompatible polymers such as polyamides, polyphosphazenes, polypropylfumarates, synthetic poly(amino acids), polyethers, polyacetals, polycyanoacrylates, polyacrylamides, polyurethanes, polycarbonates, polyanhydrides, poly(ortho esters), polyhydroxyacids, polyesters, ethylene-vinyl acetate polymers, cellulose acetates, polystyrenes, poly(vinyl chloride), poly(vinyl fluoride), poly(vinyl imidazole), poly(vinyl alcohol), chlorosulphonated polyolefins, and combinations thereof or combinations thereof with poly(meth)acrylates. In various embodiments, synthetic polymer layer 20 is a swellable (meth)acrylate layer. In some embodiments, swellable (meth)acrylate layer is formed from a hydrophilic monomer, a carboxyl group containing monomer, and a crosslinking monomer. One example of a swellable (meth)acrylate layer may be formed from hydroxyethyl methacrylate, 2-carboxyethylacrylate, and tetra(ethylene glycol) dimethacrylate. For example, the swellable (meth)acrylate may be formulated using the following liquid aliquots of monomers (by volume): hydroxyethyl methacrylate (70-90), 2-carboxyethylacrylate (10-30), and tetra(ethylene glycol) dimethacrylate (1-10). Additional details regarding suitable swellable (meth)acrylate layers are described in U.S. patent application Ser. No. 12/362,924, entitled "Synthetic Surfaces for Culturing Undifferentiated Stem Cells in Chemically Defined Media", naming Zhou et al. as inventors, and filed on even date herewith, which application is hereby incorporated herein by reference in its entirety to the extent that it does not conflict with the present disclosure.

Figure 1B:
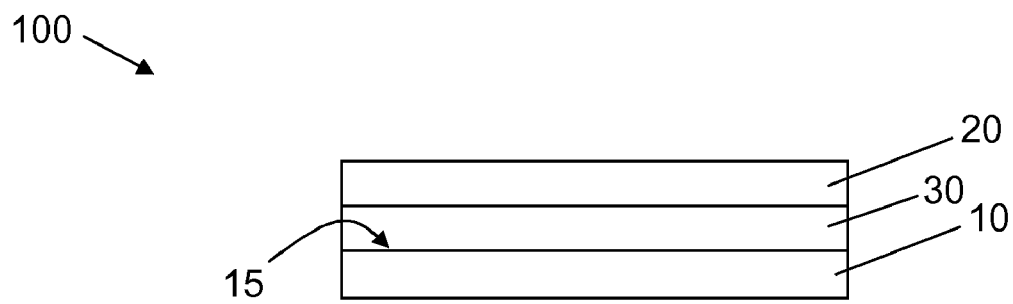

As shown in FIG. 1B, an intermediate layer 30 may be disposed between surface 15 of cell culture substrate or base material 10 and the synthetic polymer coating 20. Intermediate layer 30 may be configured to improve binding of coating 20 to substrate 10, to facilitate monomer spreading, to render portions of the cell culture surface or base material 10 that are uncoated and non-adhesive to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with an epoxy coating. For various polymer base materials 10 it may be desirable to provide an intermediate layer 30 of polyamide, polyimide, polypropylene, polyethylene, or poly(meth)acrylate. While not shown, it will be understood that synthetic polymer coating 20 may be disposed on a portion of intermediate layer 30. It will be further understood that intermediate layer 30 may be disposed on a portion of base material 10.

Figure 1C:
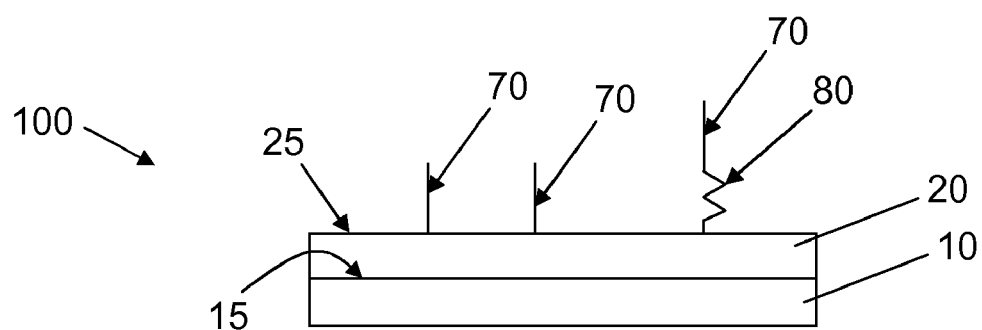

Referring now to FIG. 1C, other materials, such as polypeptides 70, may be incorporated into or conjugated to synthetic polymer surface 20, e.g. to produce a biomimetic surface. In various embodiments where polypeptides 70 are conjugated to synthetic polymer surface 20, synthetic polymer surface 20 is a hydrogel layer or a swellable (meth) acrylate layer. A linker or spacer 80, such as a repeating polyethylene glycol linker or any other suitable linker, may be used to increase distance from polypeptide 70 to surface 25 of synthetic polymer layer 20. All, some, or none of the polypeptides 70 may be conjugated to synthetic polymer layer 20 via linkers 80.

Polypeptide 70 may be conjugated to the synthetic polymer layer 20 at any density, preferably at a density suitable to support culture of cells for a desired purpose. For example, polypeptide 70 may be conjugated to synthetic polymer layer 20 at a density of between about 1 pmol per $mm^2$ and about 50 pmol per $mm^2$ of surface 25 of synthetic polymer layer 20, which can be estimated by the area of surface 15 of base material substrate 10 that is coated in embodiments where surface 15 is uniformly coated by synthetic polymer layer 20. For example, the polypeptide may be present at a density of greater than 5 $pmol/mm^2$, greater than 6 $pmo/mm^2$, greater than 7 $pmol/mm^2$ greater than 8 $pmol/mm^2$, greater than 9 $pmol/mm^2$, greater than 10 $pmol/mm^2$, greater than 12 $pmol/mm^2$, greater than 15 $pmol/mm^2$, or greater than 20 $pmol/mm^2$ of the surface of the synthetic polymer layer 20. It will be understood that the amount of polypeptide 70 present can vary depending on the composition of the synthetic polymer layer 20, the thickness of the synthetic polymer layer 20 and the nature of the polypeptide 70 itself.

In various embodiments, surface 15 of base material 10 is treated, either physically or chemically, to impart a desirable property or characteristic to the surface 15. For example, and as discussed below, surface 15 may be corona treated or plasma treated. Examples of vacuum or atmospheric pressure plasma include radio frequency RF and microwave plasmas both primary and secondary, dielectric barrier discharge, and corona discharge generated in molecular or mixed gases including air, oxygen, nitrogen, argon, carbon dioxide, nitrous oxide, or water vapor.

Synthetic polymer coating layer 20, whether disposed on an intermediate layer 30 or base material 10, preferably uniformly coats the underlying substrate. By "uniformly coated", it is meant that the layer 20 in a given area, for example a surface of a well of a culture plate, completely coats the area at a thickness of about 5 nm or greater. In embodiments, while the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

Synthetic polymer coating layer 20 may have any desirable thickness. However, it has been found that thicker coatings, e.g. coatings of greater than about 10 micrometers, tend to have unevenness around the periphery of the coating due to surface tension. In various embodiments, the thickness of the coating layer 20 is less than about 10 micrometers. For example, the thickness may be less than about 5 micrometers, less than about 2 micrometers, less than about 1 micrometers, less than about 0.5 micrometers or less than about 0.1 micrometers.

The polymer material forming synthetic polymer layer 20 may be cross-linked to any suitable degree. Low degree of crosslinking may result in partial or complete synthetic polymer layer dissolution and lower polymerization reaction efficiency. In various embodiments, the crosslinking density of synthetic polymer layer 20 is between about 0.9% and about 9%.

Figure 2A:
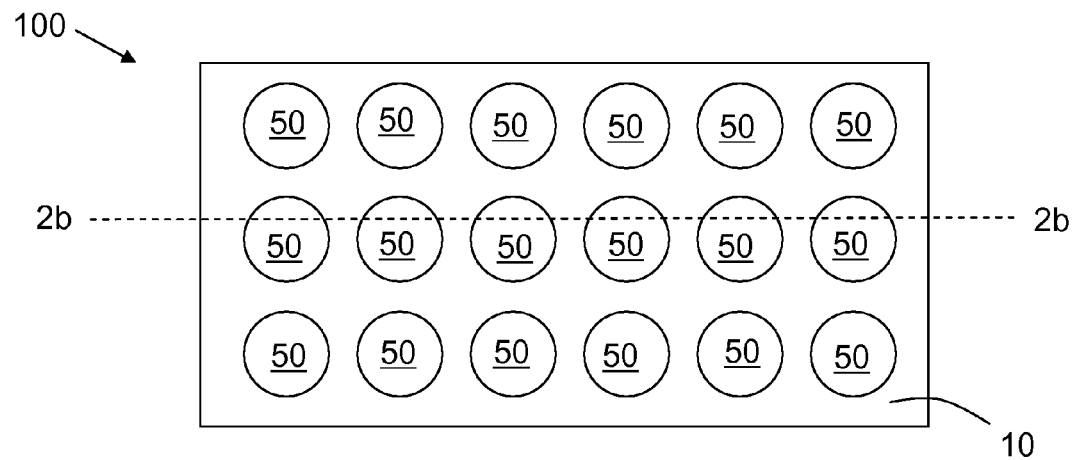
FIG. 2A is a schematic diagram of a top view of a multi-well cell culture plate.
Figure 2B:
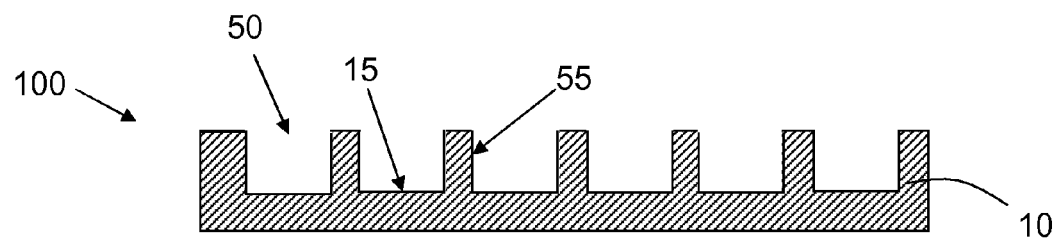
FIGS. 2B and C are schematic diagrams side views of cross sections taken through line 2b-2b of the multi-well plate depicted in FIG. 2A. The wells depicted in FIG. 2B are uncoated. The wells depicted in FIG. 2C are coated with a synthetic polymer.
Figure 2C:
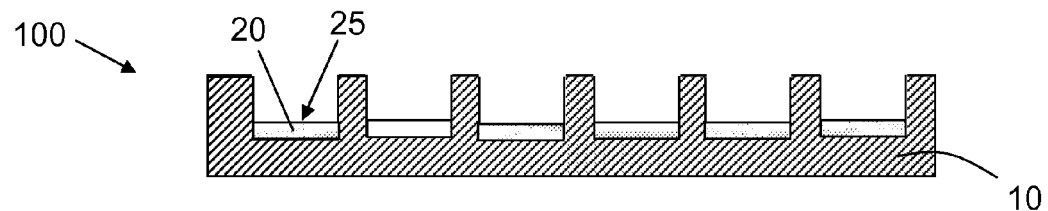

Article 100, in numerous embodiments, is traditional cell culture ware, such as a Petri dish, a multi-well plate, a slide, a flask, a multi-layer flask, a bead, a bioreactor, a bag and a beaker or other item having a surface suitable for cell culture. Referring now to FIG. 2, article 100 formed from base material 10 may include one or more wells 50. Well 50 includes a sidewall 55 and a surface 15. A synthetic polymer coating 20 may be disposed on surface 15 (or, as discussed above with regard to FIG. 1 one or more intermediate layer 30 may be disposed between surface 15 and synthetic polymer coating 20). While not shown, it will be understood that sidewall 55 may be coated with synthetic polymer layer 20. While a well is shown in FIG. 2 for illustrative purposes, it will be understood that synthetic polymer layer 20 may be on any surface suitable for cell culture.

In various embodiments, article 100 includes a uniformly coated layer 20 having a surface 25 with an area greater than about 5 $mm^2$. Of course, the surface 25 may be of any suitable size. However, when the area of the surface 15 is too small, reliable cell responses may not be readily observable because some cells, such as human embryonic stem cells, are seeded as colonies or clusters of cells (e.g., having a diameter of about 0.5 mm) and adequate surface area is desirable to ensure attachment of sufficient numbers of colonies to produce a quantitative cell response. In numerous embodiments, an article 100 has a well 50 having a uniformly coated surface 15, where the surface 15 has an area greater than about 0.1 $cm^2$, greater than about 0.3 $cm^2$, greater than about 0.9 $cm^2$, or greater than about 1 $cm^2$.

When article 100 is used for purposes of screening; e.g. as described below in more detail, article 100 preferably contains a plurality of wells 50. Different wells 50 may include synthetic polymer coating layers 20 having different thicknesses, formed from different monomers or combinations of monomers, or the like, to facilitate screening of the response of cells to the different layers 20. Of course, some wells 50 may contain no synthetic polymer layers 20 or may contain other substrates for cell culture, such as MATRIGEL™ or the like, to serve as negative or positive controls.

In embodiments, the synthetic polymer layer may be a swellable (meth)acrylate (SA) layer. In various embodiments, the synthetic polymer layer may be attached to a surface of a cell culture article. For the purposes of this disclosure, "attached" means coated on or layered on a base material or substrate so that the synthetic polymer layer does not delaminate from the base material upon exposure to normal cell culture conditions including exposure to aqueous media. The synthetic polymer layer may be attached to the substrate via covalent or non-covalent interactions. Examples of non-covalent interactions that may associate the synthetic SA surface with the substrate include chemical adsorption, hydrogen bonding, surface interpenetration, ionic bonding, van der Waals forces, hydrophobic interactions, dipole-dipole interactions, mechanical interlocking, and combinations thereof 2. Coating of Synthetic Polymer Layer The discussion that follows makes reference to articles 100 and components thereof as described above with regard to FIGS. 1-2. However, it will be understood that any suitable article may be employed with regard to the methods that follow.

Figure 3:
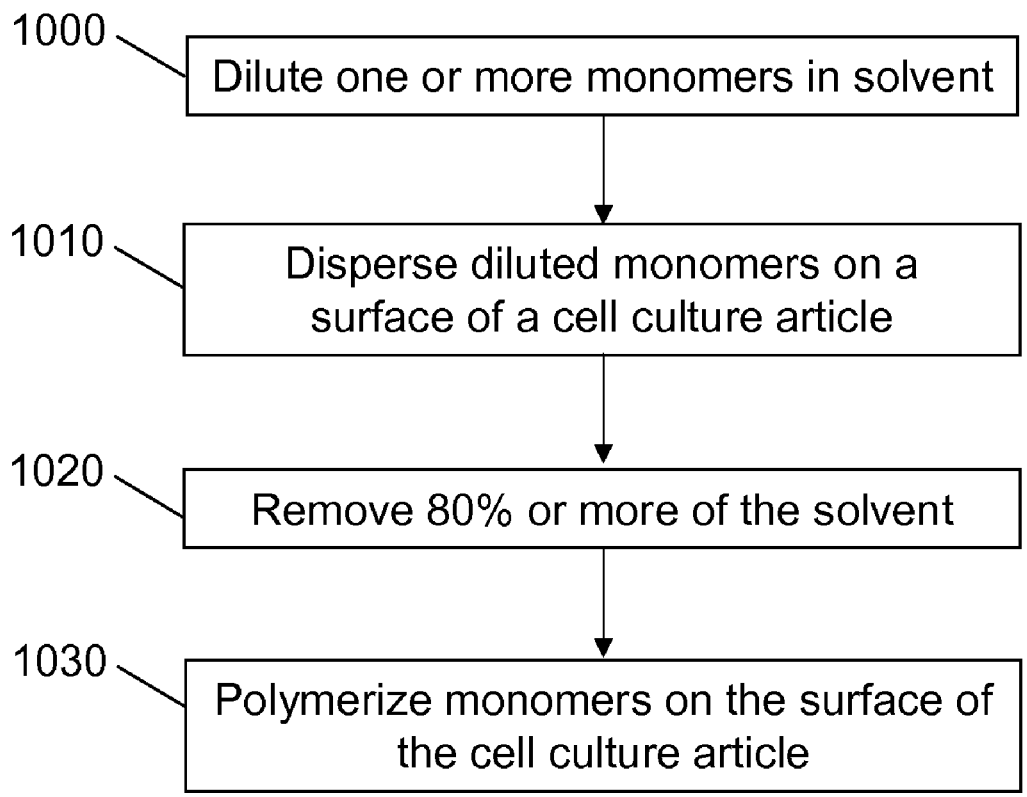
FIG. 3 is a flow diagram of representative method for producing a cell culture article having a synthetic polymer layer.

Referring now to FIG. 3, a flow diagram of a process for producing a cell culture article is shown. The method includes (1000) diluting one or more monomers in a solvent and (1010) dispersing the diluted monomers on a surface 15 of a cell culture article 100. About 80% or more of the solvent is then removed in step (1020). After removing the solvent the monomers are polymerized on the surface 15 of the article 100 in situ in step (1030). In some embodiments, about 90% or more, about 95% or more, about 99% or more, substantially all, or essentially all of the solvent is removed prior to polymerizing the monomers.

Any suitable solvent may be used in the process depicted in FIG. 3. In various embodiments, the solvent is a volatile solvent. As used herein, a volatile solvent is a solvent having a boiling point of less than about 120° C., less than about 100° C., less than about 90° C., or less than about 85° C. For example, the volatile solvent may have a boiling point between about 34° C. and about 120° C., between about 50° C. and about 100° C., or between about 70° C. and about 85° C. Examples of volatile solvents include acetone, methanol, ethyl acetate, ethanol, butanone, acetonitrile, 2-propanol, and 2-butanol. A volatile solvent preferably is readily evaporatable at room temperature, compatible with the monomers used to generate the synthetic polymer surface, non-interfering with free-radical polymerization, and non-toxic to cells to be cultured. A volatile solvent may include a non-volatile component, such as dimethyl formamide or dimethyl sulfoxide. When a volatile solvent includes a non-volatile component, the non-volatile component is preferably kept to an amount of less than about 10% by volume. A solvent used in accordance with a method as described herein is preferably a poor solvent for the base material 10 of the culture ware article 100.

A representative example of suitable class of volatile solvents is ethanol solvents. As used herein, "ethanol solvent" means a solvent having greater than about 75% ethanol. For example, an ethanol solvent may contain greater than 80%, greater than 90%, greater that 95%, greater than 97%, or greater than 99% ethanol. In various embodiments, the ethanol solvent consists essentially of ethanol. In some embodiments, an ethanol solvent consists essentially of ethanol and water. The use of an ethanol solvent may provide one or more advantages over the use of no solvent. For example, use of an ethanol solvent reduces monomer viscosity, making it possible to use automated instrumentation in the formulation process. Efficiency has been increased ten fold relative to use of no solvent, making it possible to do high throughput material screening. Use of an ethanol solvent promotes monomer spreading to achieve a thin and uniform coating for small or large surface areas using automated liquid handling instrumentation and increases coating efficiency. Use of an ethanol solvent also reduces the amount of monomer used for the coating process and may reduce final coating thickness. This can reduce cost by reducing consumption of monomers while reducing stress in coating during polymerization and swelling after contact with culture medium and finally reduces coating de-lamination. Compared to other solvents, ethanol solvents are more likely to be safe for the manufacture of cell culture ware for therapeutic cells or tissues, as ethanol solvents have been used in biomedical and pharmaceutical processes. Further, ethanol solvents are commercially available in USP grade, are easy to evaporate or otherwise remove during coating process without extreme conditions such as extreme vacuum or heat, are good solvents for a large majority of (meth)acrylate monomers while being a poor solvent form many polymers used in cell culture ware base material. In addition, ethanol appears to be relatively inert during free radical polymerization. Therefore, side effects of an ethanol solvent on the subsequent polymerization of the coating have been found to be minimal. 2-propanol solvents share many of the above-described advantages of ethanol solvents.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol solvent to provide a composition having between about 0.1% and about 50% monomer, from about 0.01% to about 10% monomer by volume, from about 0.1% to about 5% monomer by volume, or from about 0.1% to about 1% monomer by volume. The monomers may be diluted with solvent so that the polymer layer 20 achieves a desired thickness. As discussed above, if the deposited monomers are too thick, a non-uniform surface may result and the coating may likely de-laminate after contact with an aqueous medium. As described in further details in the Examples, non-uniform surfaces may be observed when the monomer-solvent composition is deposited on a surface 15 of a well 50 at a volume of greater than about 8 microliters per square centimeter of the surface 15. In various embodiments, the monomer-solvent compositions are deposited on a surface 15 of a well 50 in a volume of about 15 microliters or less per square centimeter of the surface 15. For example, the monomer-solvent compositions may be deposited on a surface 15 of a well 50 in a volume of about 7 microliters or less per square centimeter of the surface 15, or about 3 microliters or less per square centimeter of the surface 15.

In various embodiments, synthetic polymer surface 20 is produced by depositing one or more monomers on a surface 15 of a base material 10 and then polymerizing the one or more monomers in situ. In such embodiments, the base material 10 will be referred to herein as the "substrate" on which the synthetic polymer material 20 is deposited. The synthetic polymer surface 20 may be associated with the base material surface 15 via covalent or non-covalent interactions. Examples of non-covalent interactions that may associate the synthetic polymer surface with the substrate include chemical adsorption, hydrogen bonding, surface interpenetration, ionic bonding, van der Waals forces, hydrophobic interactions, dipole-dipole interactions, mechanical interlocking, and combinations thereof.

In various embodiments, synthetic polymer surface 20 is deposited on a surface of an intermediate layer 30 that is associated with the base material 10 via covalent or non-covalent interactions, either directly or via one or more additional intermediate layers (not shown). In such embodiments, the intermediate layer 30 will be referred to herein as the "substrate" onto which the synthetic polymer surface 20 is deposited.

In various embodiments, the surface 15 of the base material 10 is treated. The surface 15 may be treated to improve binding of the synthetic polymer surface 10 to the base material surface 15, to facilitate monomer spreading on the base material surface 15, or the like. Of course, the base material 10 may be treated for similar purposes with regard to an intermediate layer 30. In various embodiments, the surface is corona treated or plasma treated. High surfaces energy obtainable from such treatments may facilitate monomer spreading and uniform coating.

It has been found that plasma treatment, compared to corona treatment of substrate formed from cyclic olefin copolymers, leads to better wettability for monomers (see Table 1), which facilitates spreading of the monomers. In addition, it has been found that the effects on wettability of plasma treatment last longer than that of corona treatment (data not shown). For example, plasma treated surfaces can be used more than one week after treatment, while corona treated surfaces are generally ineffective unless used soon after treatment.

TABLE 1

Related wetting properties of selected (meth)acrylate monomers on plasma or corona discharge treated cyclic olefin surface.

| Monomers | Plasma | Corona Discharge |
|---|---|---|
| TEGDA | ++++ | +++ |
| GDM | ++ | ++ |
| TriEGDM | ++++ | ++ |
| BDM | +++ | + |
| PEGDA | ++++ | +++ |

For the data presented in Table 1, cyclic olefin surfaces were vacuum plasma treated as described in Example 1 below (TEGDA: tetra(ethylene glycol) diacrylate; GDM: glycerol dimethacrylate; TriEGDM: Triethylene glycol dimethacrylate; BDM: 1,4-butanediol dimethacrylate; PEGDA: poly(ethylene glycol) diacrylate, $M_n \sim 258$).

To form the synthetic polymer surface, one or more monomers may be polymerized in situ. If one monomer is used, the polymer will be referred to as a homopolymer of the monomer. If two or more different monomers are used, the polymer will be referred to as a copolymer of the monomers. The monomers employed may be monofunctional, difunctional, or higher-functional. When two or more monomers are used, the ratio of the monomers may be varied. In various embodiments, two monomers are used and the ratio, by volume of the first monomer to the second monomer ranges from between about 5:95 to about 95:5. For example, the ratio of the first monomer to the second monomer ranges from between about 10:90 to about 90:10, about 20:80 to about 80:20, from about 30:70 to about 70:30. In some embodiments, the ratio of the first monomer to the second monomer is about 50:50, 30:70, or 10:90. If one or more of the monomers are not liquids at room temperature, the above ratios may be employed on a weight basis.

In addition to the monomers that form the polymer layer, composition forming the layer may include one or more additional compounds such as surfactants, wetting agents, photoinitiators, thermal initiators, catalysts, activators, and cross-linking agents.

In numerous embodiments, the synthetic polymer surface 20 is a poly(meth)acrylate surface. Any suitable (meth)acrylate monomer or combination of monomers may be employed to form the poly(meth)acrylate to form the synthetic layer 20. As used herein, a "(meth)acrylate monomer" means a compound having at least one ethylenically unsaturated moiety (an acrylate moiety or a methacrylate moiety). "Poly(meth)acrylate", as used herein means a polymer formed from one or more monomers including at least one (meth)acrylate monomer. Examples of monomers that may be used to form poly(meth)acrylates include those listed in Table 2.

TABLE 2

Listing of some example (meth)acrylate monomers

| Name | Structure |
|---|---|
| Tetra(ethylene glycol) diacrylate | $\left(H_2C=CH-\overset{O}{\underset{\|}{C}}-OCH_2CH_2OCH_2CH_2\right)_2 O$ |
| Glycerol dimethacrylate | $H_2C=\overset{CH_3}{\underset{\|}{C}}-\overset{O}{\underset{\|}{C}}-OCH_2\overset{OH}{\underset{\|}{CH}}CH_2-O-\overset{O}{\underset{\|}{C}}-\overset{CH_3}{\underset{\|}{C}}=CH_2$ |
| Triethylene glycol dimethacrylate | $H_2C=\overset{\underset{CH_3}{\|}}{\underset{\|}{C}}-\overset{O}{\underset{\|}{C}}-(OCH_2CH_2)_3O-\overset{O}{\underset{\|}{C}}-\overset{CH_3}{\underset{\|}{C}}=CH_2$ |
| 1,4-Butanediol dimethacrylate | $H_2C=\overset{\underset{CH_3}{\|}}{\underset{\|}{C}}-\overset{O}{\underset{\|}{C}}-OCH_2CH_2CH_2CH_2O-\overset{O}{\underset{\|}{C}}-\overset{\underset{CH_3}{\|}}{\underset{\|}{C}}=CH_2$ |
| Poly(ethylene glycol) diacrylate (average $M_n \sim 258$) | $H_2C=CH-\overset{O}{\underset{\|}{C}}-(OCH_2CH_2)_n-O-\overset{O}{\underset{\|}{C}}-CH=CH_2$ |

TABLE 2-continued

Listing of some example (meth)acrylate monomers

| Name | Structure |
|---|---|
| Di(ethylene glycol) dimethacrylate | $H_2C{=}C(CH_3){-}C(O){-}OCH_2CH_2OCH_2CH_2O{-}C(O){-}C(CH_3){=}CH_2$ |
| Tetra(ethylene glycol) dimethacrylate | $H_2C{=}C(CH_3){-}C(O){-}OCH_2CH_2OCH_2CH_2OCH_2CH_2OCH_2CH_2O{-}C(O){-}C(CH_3){=}CH_2$ |
| 1,6-Hexanediol propoxylate diacrylate | $H_2C{=}CH{-}C(O){-}O{-}(C_3H_6O)_n{-}CH_2CH_2CH_2{-}$ (bonded to central C), $H_2C{=}CH{-}C(O){-}O{-}(C_3H_6O)_n{-}CH_2CH_2CH_2{-}$ |
| Neopentyl glycol diacrylate | $H_2C{=}CH{-}C(O){-}OCH_2{-}C(CH_3)_2{-}CH_2O{-}C(O){-}CH{=}CH_2$ |
| Neopentyl glycol dimethacrylate | $H_2C{=}C(CH_3){-}C(O){-}OCH_2{-}C(CH_3)_2{-}CH_2O{-}C(O){-}C(CH_3){=}CH_2$ |
| Trimethylolpropane benzoate diacrylate | $H_2C{=}CH{-}C(O){-}OCH_2{-}C(CH_2CH_3)(CH_2O{-}C(O){-}C_6H_5){-}CH_2O{-}C(O){-}CH{=}CH_2$ |
| Trimethylolpropane ethoxylate (1 EO/OH) methyl diacrylate | $H_2C{=}CH{-}C(O){-}OCH_2CH_2OCH_2{-}C(CH_2CH_3)(CH_2OCH_2CH_2OCH_3){-}OCH_2CH_2OCH_2{-}C(O){-}CH{=}CH_2$ |
| Tricyclo[5.2.1.0$^{2,6}$]decanedimethanol diacrylate | $H_2C{=}CH{-}C(O){-}O{-}CH_2{-}[tricyclodecane]{-}CH_2{-}O{-}C(O){-}CH{=}CH_2$ |
| Neopentyl glycol ethoxylate diacrylate (Ph4160 from Cognis) | $CH_2{=}CH{-}C(O){-}(O{-}CH_2CH_2)_x{-}O{-}CH_2{-}C(CH_3)_2{-}CH_2{-}O{-}(CH_2CH_2{-}O)_y{-}C(O){-}CH{=}CH_2$ |
| Trimethylolpropane triacrylate | $H_2C{=}CH{-}C(O){-}OCH_2{-}C(CH_2CH_3)(CH_2O{-}C(O){-}CH{=}CH_2)_2$ |

TABLE 2-continued

Listing of some example (meth)acrylate monomers

| Name | Structure |
|---|---|
| 1,6-Hexanediol diacrylate | $\left(H_2C=CH-\overset{O}{\underset{\|}{C}}-OCH_2CH_2CH_2-\right)_2$ |
| Neopentyl glycol propoxylate (1PO/OH) diacrylate | $H_2C=CH-\overset{O}{\underset{\|}{C}}-O(C_3H_6O)_mCH_2-\overset{CH_3}{\underset{CH_3}{\overset{\|}{C}}}-CH_2(OC_3H_6)_nO-\overset{O}{\underset{\|}{C}}-CH=CH_2$<br>$m + n \sim 2$ |
| Glycerol 1,3-diglycerolate diacrylate | $H_2C=CH-\overset{O}{\underset{\|}{C}}-OCH_2CHCH_2OCH_2CHCH_2OCH_2CHCH_2O-\overset{O}{\underset{\|}{C}}-CH=CH_2$<br>$\qquad\qquad\qquad OH\qquad OH\qquad OH$ |
| 1,6-Hexanediol ethoxylate diacrylate $M_n \sim 314$ | $H_2C=CH-\overset{O}{\underset{\|}{C}}-O-(CH_2CH_2O)_n-CH_2CH_2CH_2$<br>$H_2C=CH-\overset{O}{\underset{\|}{C}}-O-(CH_2CH_2O)_n-CH_2CH_2CH_2$ |
| 2,2,3,3,4,4,5,5 octafluoro 1,6 hexanediol diacrylate | (structure with F F F F / F F F F fluorinated chain between two acrylate groups) |
| Poly(propylene glycol) diacrylate | $H_2C=CH-\overset{O}{\underset{\|}{C}}-(OC_3H_6)_n-O-\overset{O}{\underset{\|}{C}}-CH=CH_2$<br>$n \sim 7$ |
| 1,9 nonanediol diacrylate | (diacrylate of 1,9-nonanediol) |
| Neopentyl glycol methyl ether propoxylate (2PO/OH) acrylate | $H_2C=CH-\overset{O}{\underset{\|}{C}}-O\overset{CH_3}{\underset{\|}{C}}HCH_2O\overset{CH_3}{\underset{\|}{C}}HCH_2OCH_2-\overset{CH_3}{\underset{CH_3}{\overset{\|}{C}}}-CH_2OCH_3$ |
| N-(Isobutoxymethyl) acrylamide | (acrylamide with -NH-CH_2-O-CH_2-CH(CH_3)_2) |
| 2-Hydroxyethyl methacrylate | (methacrylate of ethylene glycol) |
| Ethylene glycol phenyl ether methacrylate | (methacrylate -O-CH_2CH_2-O-phenyl) |

TABLE 2-continued

Listing of some example (meth)acrylate monomers

| Name | Structure |
| --- | --- |
| 2-Carboxyethyl acrylate | 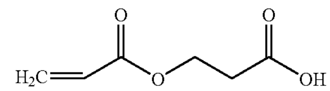 |
| 2-Hydroxyethyl acrylate | 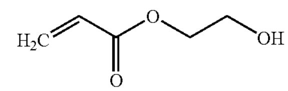 |
| Hydroxybutyl methacrylate, mixture of isomers | 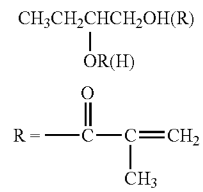 |
| 2-(Dimethylamino)ethyl methacrylate | 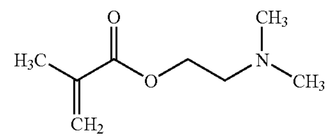 |
| Benzyl methacrylate | 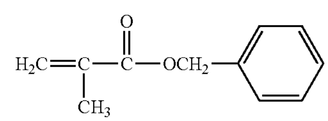 |
| Isobutyl acrylate | 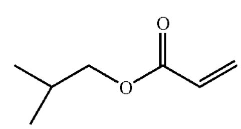 |

Of course, any other suitable (meth)acrylate monomer may be used. One or more (meth)acrylate monomer is used to form the synthetic polymer layer. Many (meth)acrylate polymers are commercially available from, e.g., Polysciences, Inc., Sigma Aldrich, Inc., and Sartomer, Inc.

In various embodiments, the synthetic layer is formed from a composition comprising one or more (meth)acrylate monomers, where at least one of the one or more monomers is glycerol dimethacrylate.

Regardless of the monomers used, the properties of the resulting polymers may be adjusted. For example, ester and ether groups, to different degrees, contribute to the hydrophilicity of the resulting polymer, and thus the amounts of such groups can be varied to vary hydrophilicity. In addition, the use of amino, thio, or oxygenated groups may be employed in desired amounts to vary the electron density of the resulting polymer. Further, by varying the number of ether groups in the monomer and the distance between the ester linkages, the electron density of the polymer may be readily tailored. Branched monomers also change electron density by allowing more ether groups to fit in a certain length or by changing the packing density of the resulting polymer. The use of cyclic moieties and aromatic moieties also affects electron density. In addition, the cross-link density of the polymer may be adjusted by varying the proportion of multifunctional, such as bi- or tri-functional monomers to monofunctional monomers.

The molecular weight of the polymer may be controlled by varying the concentration of monomer in the stock solution or the ratios of difunctional or higher-functional monomers to monofunctional monomers. Increased concentrations of difunctional or higher-functional monomers will increase the degree of cross-linking in the chains. Monofunctional monomers may be modified to form difunctional monomers by reacting them with a linker chain. Appropriate linkers and chemical reactions will be evident to one skilled in the art. For example, dicarboxylic acids are reactive with a wide variety of functional groups commonly incorporated into vinyl monomers, including alcohols, amines, and amides.

As described herein volatile solvents are preferably employed. When using volatile solvents, monomers that polymerize by chain polymerization are preferred relative to monomers that polymerize by step polymerization. However, step polymerization monomers may be employed in various embodiments.

For monomers that polymerize via chain polymerization, such as (meth)acrylates, any suitable initiator may be employed and added to the monomer mixture. One of skill in the art will readily be able to select a suitable initiator, e.g. a radical initiator, an anionic initiator, or a cationic initiator, based on the monomers being used to form the synthetic polymer substrate. For (meth)acrylates, radical initiators or cationic initiators may be employed. In various embodiments, UV light is used to generate free radical monomers to initiate chain polymerization.

Any suitable initiator may be used. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.).

A photosensitizer may also be included in a suitable initiator system. Representative photosensitizers have carbonyl groups or tertiary amino groups or mixtures thereof. Photosensitizers having a carbonyl group include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators include salts of onium cations, such as arylsulfonium salts, as well as organometallic salts such as ion arene systems.

Following dilution of the selected monomers, the diluted monomers may be deposited on the substrate. When performing high throughput screening, it may be desirable to use automated processes for depositing the diluted monomers on the substrate. An example of a suitable automated dispenser is the BioTek PRECISION Microplate Pipetting System (BioTek Instruments, Inc.). Once stock compositions of the diluted monomers have been prepared, they may be loaded into separate reservoirs of a robotic liquid handling device.

Regardless of whether automated processes and equipment are used, it will be understood that the amount and concentration of diluted monomer composition applied to the substrate surface may be controlled to control the thickness of the eventual synthetic polymer layer. It will be further understood that by reducing the viscosity of the monomers through dilution, a thinner layers having uniformity may be produced, allowing for use of less monomer material.

Following deposition of the monomers on the substrate surface, the solvent may be removed prior to polymerizing. The solvent may be removed by any suitable mechanism or process. Preferably, the solvent is removed by evaporation. In various embodiments, the solvent is removed by evaporation at room temperature and ambient pressure under air or nitrogen. For volatile solvents having a boiling point of about 80° C. or less, about one hour or more under such conditions is typically capable of removing a significant amount of solvent. In some embodiments, mild vacuum or elevated temperatures may be employed speed the evaporation process. In some embodiments, e.g. where it is not desired to wait for evaporation, the additional step of removing solvent may be omitted before curing. In such situations, some solvent may evaporate during the curing process.

By removing substantially all of the solvent prior to curing, curing kinetics and the amount of converted monomer can be better controlled. Generally, removing about 80% or more of the solvent should be sufficient to better control curing. In some embodiments, about 90% or more, about 95% or more, or about 99% or more of the solvent is removed prior to curing. When conversion rates of the monomers are increased, waste generation and cytotoxicity are reduced.

In various embodiments, the monomers are sprayed onto the substrate surface. Spraying may be performed using air pressure sprayers or electronic sprayers generally known in the art. Spraying may allow for more rapid evaporation of solvent and provide uniform thin synthetic polymeric surfaces. In additional embodiments, the monomers may be applied to the substrate surface by liquid application, dip coating or spin coating.

Following removal of substantially all of the solvent, the monomers are polymerized via an appropriate initiation mechanism. For example, temperature may be increased to activate a thermal initiator, photoinitiators may be activated by exposure to appropriate wavelength of light, or the like. According to numerous embodiments, the monomer or monomer mixture is cured using UV light. The curing preferably occurs under inert gas protection, such as nitrogen protection, to prevent oxygen inhibition. Suitable UV light combined with gas protection may increase polymer conversion, insure coating integrity and reduce cytotoxicity. A UV light, with a dose of >0.2 J/cm$^2$ at a power of 5~100 mW/cm$^2$ and for longer than 10 seconds, is one example of suitable curing conditions when using a UV photoinitiator with (meth)acrylate monomers. Too high or too low power of curing light may affect coating uniformity or conversion of curing. A mild curing process also reduces the heat during polymerization, to which the substrates may also be sensitive. In various embodiments, UV light is pulsed, using a pulsed light source or by turning the UV source on and off at controlled time intervals. For example, using a pulsed UV light, which delivers a dose of 0.8 J/cm$^2$ at a power of 13 mW/cm$^2$ in nitrogen protection, provides more uniform coating with lower cytotoxicity relative to using a higher power UV system, which delivers 1.4 J/cm$^2$ in 3 second (see Examples). In various embodiments, pulsed UV radiation at a dose of between about 0.5 J/cm$^2$ and about 1.1 J/cm$^2$ at a power of between about 5 mW/cm$^2$ and about 100 mW/cm$^2$, e.g. about 10 mW/cm$^2$, is delivered. In other embodiments a UV source, with a dose of >0.2 J/cm$^2$ at a power of 5~100 mW/cm$^2$ and for longer than 10 seconds is used to cure the synthetic polymer layer 20.

The cured synthetic polymer layer 20 may be washed with solvent one or more times to remove impurities such as unreacted monomers or low molecular weight polymer species. In various embodiments, the layer 20 is washed with an ethanol solvent, e.g. greater than about 70% ethanol, greater than about 90% ethanol or greater than about 99% ethanol. Washing with an ethanol solvent will not only serve to remove impurities, which may be cytotoxic, but also can serve to sterilize the surface prior to incubation with cells.

A polypeptide may be conjugated to a synthetic polymer layer 20 via any suitable technique. A polypeptide may be conjugated to a synthetic polymer layer 20 via an amino terminal amino acid, a carboxy terminal amino acid, or an internal amino acid. One suitable technique for conjugating polypeptides to synthetic polymer layers involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of a hydrogel or swellable (meth)acrylate layer to produce amine reactive NHS esters. EDC reacts with a carboxyl group of the swellable (meth)acrylate layer or synthetic polymer layer 20 to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for two step procedures. Following activation of the synthetic polymer layer 20, the polypeptide 70 may then be added and the amino-terminal amine of the polypeptide 70 can react with the amine reactive ester to form a stable amide bond, thus conjugating the polypeptide 70 to the synthetic polymer layer 20. When EDC/NHS chemistry is employed to conjugate polypeptide 20 to synthetic polymer layer 20, the N-terminal amino acid is preferably an amine containing amino acid such as lysine, homolysine, ornithine, diaminobutyric acid, or diaminoproprionic acid. In addition, the N-terminal alpha amine of a polypeptide may be used to conjugate to the carboxyl group, if the N-terminal amine is not capped. Of course, any acceptable nucleophile may be employed, such as hydroxylamines, hydrazines, hydroxyls, and the like.

EDC/NHS chemistry results in a zero length crosslinking of the polypeptide 70 to the synthetic polymer layer 20. Linkers 80 or spacers, such as polyethylene glycol linkers (e.g., available from Quanta Biodesign, Ltd.) with a terminal amine may be added to the N-terminal amino acid of peptide 70. When adding a linker to the N-terminal amino acid, the linker is preferably a N-PG-amido-PEG$_x$-acid where PG is a protecting group such as the Fmoc group, the BOC group, the CBZ group or any other group amenable to peptide synthesis and X is 2, 4, 6, 8, 12, 24 or any other discrete PEG which may be available.

In various embodiments, a 1 µM-2500 µM polypeptide fluid composition, such as a solution, suspension, or the like, is contacted with an activated synthetic polymer layer to conjugate the polypeptide. For example the polypeptide concentration may be between about 100 µM and about 2000 µM, between about 500 µM and about 1500 µM, or about 1000 µM. It will be understood that the volume of the polypeptide composition and the concentration may be varied to achieve a desired density of polypeptide conjugated to the synthetic polymer layer.

The polypeptide may be cyclized or include a cyclic portion. Any suitable method for forming cyclic polypeptide may be employed. For example, an amide linkage may be created by cyclizing the free amino functionality on an appropriate amino-acid side chain and the a free carboxyl group of an appropriate amino acid side chain. Alternatively, a di-sulfide linkage may be created between free sulfhydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. In various embodiments, the polypeptide is a multi-antigen polypeptide having peptide dendrimers.

A linker or spacer, such as a poly(ethylene oxide) linker, may be conjugated to incorporated into the polypeptide to project the polypeptide away from the surface using any suitable linker and any suitable technique.

In various embodiments, the polypeptide is derived from a naturally occurring cell adhesion polypeptide, such as fibronectin, laminin, vitronectin, or the like. In some embodiments, the polypeptide contains an RGD amino acid sequence. Examples of some suitable RGD-containing polypeptides are described in U.S. patent application Ser. No. 12/362,924, entitled "Synthetic Surfaces for Culturing Undifferentiated Stem Cells in Chemically Defined Media", naming Zhou et al. as inventors, and filed on even date herewith.

3. Screening of Synthetic Polymer Layers for Desirable Cell Interaction

The discussion that follows makes reference to articles 100 and components thereof as described above with regard to FIGS. 1-2. However, it will be understood that any suitable article may be employed with regard to the methods that follow.

Figure 4:
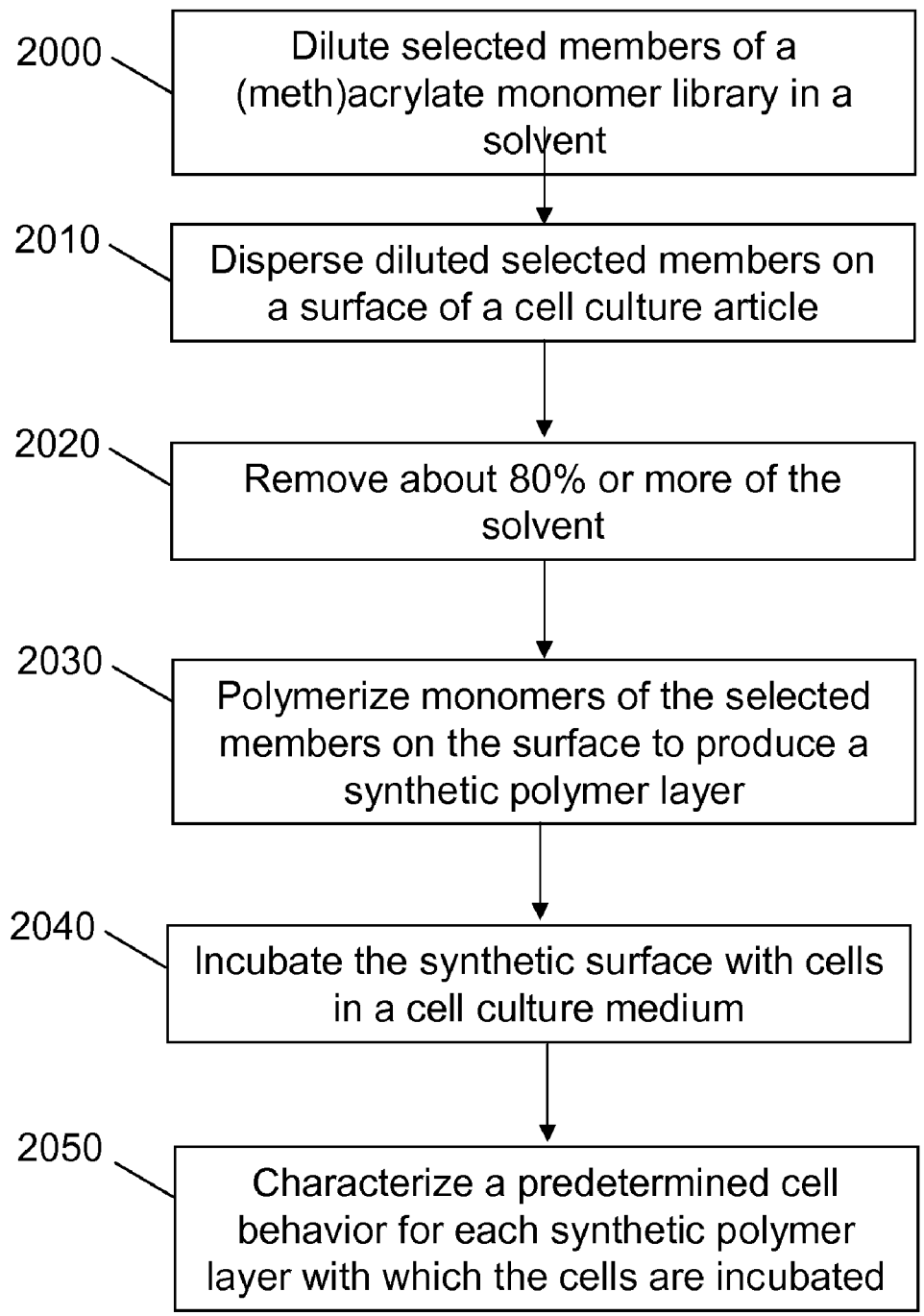
FIG. 4 is a flow diagram of a representative method for screening cell interactions with synthetic polymer layers.

Referring now to FIG. 4, a flow diagram of a screening method is depicted. The depicted method is similar, in many aspects, to the method depicted in FIG. 3 as described above. The method includes (2000) the step of diluting selected members of a monomer library in a solvent. In embodiments, the solvent may be a volatile solvent like an ethanol solvent. The method includes (2010) the step of dispersing the diluted selected members on substrate of an article 100 for cell culture. As used herein, "diluting a selected member of a monomer library" or the like, means diluting one or more monomers in a solvent, either as a single composition or as a plurality of compositions with different one or more monomers of the selected members diluted as separate compositions. A member of the library may include a single monomer or may include two or more monomers. When one or more of the selected members are diluted separately in the solvent as separate compositions, the separate compositions may be combined when dispersed on the substrate or prior to dispersing on the substrate. It may be desirable to generate stock compositions of individual monomers diluted in solvent and then combining the stock compositions on the substrate or prior to dispersing on the substrate. Such stock solutions may be advantageous when using automated equipment to generate an array in, for example, a multi-well plate useful for screening.

While FIG. 4 depicts a (meth)acrylate monomer library, it will be understood that a library of any other suitable monomer may also be employed.

The method depicted in FIG. 4 includes (2020) the step of removing about 80% or more of the solvent after the selected members of the library are dispersed on the substrate. In some embodiments, substantially all of the solvent is removed. As used herein, "removing substantially all of the solvent" or the like means removing a sufficient amount of the solvent to allow for polymerization of the monomers. If the monomers are highly diluted; e.g. about 99% solvent to 1% monomer (by volume) to allow for a thin uniform coating, it may be desirable to remove a sufficient amount of solvent to provide a high enough concentration of monomer(s) to allow for sufficient polymerization. That is, the higher the concentration of monomers, the closer the monomers will be to neighboring monomers, allowing for more polymerization. Residual solvent may also facilitate monomer movement toward free radials nearby during polymerization, which will promote the completion of polymerization and increase final conversion.

Embodiments of the present invention provide a method for screening cell-synthetic polymer layer interactions, comprising: diluting, in a solvent, one or more (meth)acrylate monomers to form a solution; dispersing the solution on one or more surfaces of cell culture substrates; removing about 80% or more of the solvent from the dispersed solution; polymerizing the meth)acrylate monomers after removing the about 80% or more of the solvent to form a synthetic polymer layer on the one or more surfaces; incubating the synthetic polymer layers with cells in a cell culture medium; and characterizing a predetermined cell behavior for each synthetic polymer layer with which the cells are incubated. In embodiments, the step of removing the solvent comprises evaporating the solvent from the one or more surfaces. In embodiments, the cells may be any cell type, and may be stem cells, human embryonic stem cells, pluripotent cells or adult stem cells. In embodiments the substrate or surface may be plasma treated prior to dispersing the solution. In embodiments, polymerizing the monomers comprises exposing the monomers to UV radiation including pulsed UV radiation. In embodiments, the pulsed UV radiation is delivered at a dose of between about 0.5 J/cm$^2$ and about 1.1 J/cm$^2$ at a power of between about 5 mW/cm$^2$ and about 100 mW/cm$^2$ is delivered. In embodiments, exposing the monomers to UV radiation comprises exposing the monomers to radiation in nitrogen. In embodiments, polymerizing the monomers on the one or more surfaces to form the synthetic polymer layer comprises forming a swellable (meth)acrylate layer. In embodiments, the method further comprising conjugating a polypeptide to the swellable (meth)acrylate layer. In embodiments, at least one of the selected monomers is glycerol dimethacrylate.

The method depicted in FIG. 4 further includes (2030) the step of polymerizing the monomers dispersed on the substrate, after about 80% or more of the solvent is removed, to produce a synthetic polymer layer e.g. as described above. Cells, such as stem cells, may then be incubated with the synthetic polymer layer in step (2040) and a predetermined behavior of the cells may be characterized in step (2050) for each synthetic polymer layer 20 with which the cells are incubated.

A. Incubating Cells on Synthetic Polymer Layer

A substrate coated with a synthetic polymer layer 20 as described above may be seeded with cells. The cells may be of any cell type. For example, the cells may be connective tissue cells such as epithelial and endothelial cells, hepatocytes, skeletal or smooth muscle cells, heart muscle cells, intestinal cells, kidney cells, or cells from other organs, stem cells, islet cells, blood vessel cells, lymphocytes, cancer cells, or the like. The cells may be mammalian cells, preferably human cells, but may also be non-mammalian cells such as bacterial, yeast, or plant cells.

In numerous embodiments, the cells are stem cells. As used herein, "stem cell" means a cell that has the ability to continuously divide (self renewal) and capable of differentiating into diverse range of specialized cell types. In some embodiments, the stem cells may be multipotent, totipotent, or pluripotent stem cells. The stem cells may be present in an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoietic stem cell. A stem cell may be a multi-lineage cell derived from epithelial and adipose tissues, umbilical cord blood, liver, brain or other organ.

Because human embryonic stem cells (hESC) have the ability to grown continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hESBGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

Other suitable stem cells include induced primate pluripotent (iPS) stem cells OPCs according to the invention may also be differentiated from induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm and thus are suitable for differentiation into a variety of cell types. The iPS cells, like hESC, also form teratomas when injected into immuno-deficient mice, e.g., SCID mice. (Takahashi et al., (2007) Cell 131(5):861; Yu et al., (2007) Science 318:5858).

Prior to seeding cells, the cells may be harvested and suspended in a suitable medium, such as a growth medium in which the cells are to be cultured once seeded onto the surface. For example, the cells may be suspended in and cultured in serum-containing medium, a conditioned medium, or a chemically-defined medium. As used herein, "chemically-defined medium" means cell culture media that contains no components of unknown composition. Chemically defined media may, in various embodiments, contain no proteins, hydrosylates, or peptides of unknown composition. In some embodiments, chemically-defined media contains polypeptides or proteins of known composition, such as recombinant growth hormones. Because all components of chemically-defined media have a known chemical structure, variability in culture conditions and thus cell response can be reduced, increasing reproducibility. In addition, the possibility of contamination is reduced. Further, the ability to scale up is made easier due, at least in part, to the factors discussed above. Chemically defined cell culture media are commercially available from, for example, Invitrogen (Invitrogen Corporation, 1600 Faraday Avenue, PO Box 6482, Carlsbad, Calif. 92008) as StemPro® a fully defined, serum- and feeder-free medium (SFM) specially formulated for the growth and expansion of human embryonic stem cells (hESCs), StemCell Technologies, Inc as mTeSR™1 maintenance media for human embryonic stem cells and XVivo-10, which can be supplemented with growth factors, available from Lonza.

One or more growth or other factors may be added to the medium in which cells are incubated with the synthetic polymer layer 20. The factors may facilitate cellular proliferation, adhesion, self-renewal, differentiation, or the like. Examples of factors that may be added to or included in the medium include muscle morphogenic factor (MMP), vascular endothelium growth factor (VEGF), alpha or beta transforming growth factor (TGF), interleukins, nerve growth factor (NGF), erythropoietin, platelet derived growth factor (PDGF), epidermal growth factor (EGF), activin A (ACT), such as Activin A, hematopoietic growth factors, retinoic acid (RA), interferons, fibroblastic growth factors (FGF), such as basic fibroblast growth factor (bFGF), bone morphogenetic protein (BMP), peptide growth factors, heparin binding growth factor (HBGF), hepatocyte growth factor (HGF), tumor necrosis factors (TNF), insulin-like growth factors (IGF) I and II, transforming growth factors (TGF), such as transforming growth factor-β1 (TGFβ1), and colony stimulating factors.

The cells may be seeded at any suitable concentration. Typically, the cells are seeded at about 10,000 cells/cm$^2$ of substrate to about 500,000 cells/cm$^2$. For example, cells may be seeded at about 40,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are incubated on the surface may vary depending on the cell response being studied or the cell response desired.

B. Characterizing Predetermined Behavior

Any cell behavior that can produce desirable information regarding the interaction of cells and the synthetic surface may be characterized. For example, cell morphology or the degree or amount of (i) cell adhesion; (ii) proliferation; (iii) differentiation; (iv) pluripotency, (v) metabolic behavior, such as activity level, metabolic state, DNA synthesis, apoptosis, contraction, mitosis, exocytosis, synthesis, endocytosis, and migration; (vi) gene expression; or (vii) protein expression may be investigated to determine the nature of the interaction between the cells and the synthetic substrate.

Any suitable assay may be used for characterizing a predetermined behavior of a cell. For example, any of the cell-based assays known in the art may be used to screen for desirable interactions between the synthetic polymer layers 20 and a given cell type. When they are assayed, the cells may be fixed or living. Typically, assays on living cells involve fluorescent or chemiluminescent indicators. Alternatively or in addition, molecular-based assays that screen for interactions at a molecular level using molecular targets may also be employed.

Various protein markers may be used to determine the type or behavior of cells incubated with the synthetic polymer layers 20. By way of example, nestin and GFAP are protein markers useful in identifying cells that are differentiating as nerve cells, cytokeratin is a marker for epidermal cells, and desmin is a marker for muscle cells, Oct3/4, Tra-1-60, SSEA4, alkaline phosphatase and other stem cell specific markers may be used to assess the undifferentiated state of the stem cells. Of course, any other known or further identified protein marker may be used to identify the type or behavior of cells. Alternatively or in addition, genetic markers associated with particular cell types or cell behaviors may be used to characterize the cells incubated with the synthetic polymer layers 20.

Examples of cell based assays that may be employed for characterizing a predetermined behavior of a cell include assays that involve the use of microscopy, such as phase contrast and fluorescent microscopy, or any other method to quantitatively or qualitatively assess cell behavior, such as measurement or observation with an automated or manual device of optical density, fluorescent or luminescent measurements of specific cell response or enzyme activity. Microscopy may be performed alone or in combination with, for example, cell staining; cytochemistry, immunocytochemistry with fluorescent-labeled antibodies; fluorescence in situ hybridization (FISH) of nucleic acids; gene expression assays that involve fused promoter/reporter sequences that encode fluorescent or chemiluminescent reporter proteins; in situ PCR with fluorescently labeled oligonucleotide primers; fluorescence resonance energy transfer (FRET) based assays that probe the proximity of two or more molecular labels; and fused gene assays that enable the cellular localization of a protein of interest. The steps involved in performing such cell-based assays are well known in the art. For the purposes of clarification only, and not for limitation, certain properties and practical aspects of some of these cell-based assays are considered in greater detail in the following paragraphs.

In numerous embodiments, an automated device is used to analyze the cell-based assays for each synthetic polymer layer 20. The automated devices may be manually or automatically operated.

In various embodiments, the ability of an undifferentiated stem cell to attach and grow on a synthetic polymer layer 20 is determined. One assay for determining whether undifferentiated stem cells are present in a culture is an alkaline phosphatase (AP) assay. Alkaline phosphatase (AP) is a marker for undifferentiated hESCs. AP expression is lost or significantly reduced as cells differentiate. One suitable alkaline phosphatase assay includes fixing cells after incubating them on experimental surfaces for desired period of time (e.g., about 48 hrs), incubating the fixed cells with soluble alkaline phosphatase substrate, for example AttoPhos® substrate (2'-[2-benzothiazol]-6'-hydroxybenzothiazole phosphate [BBTP]), and obtaining AttoPhos fluorescent intensity at 485/535 nm using an appropriate plate reader, such as the Victor 3 microplate reader from Perkin Elmer. AttoPhos fluorescent intensity for experimental surfaces can be expressed as a % of positive control, such as % of MATRIGEL™ control.

Another method for determining whether undifferentiated stem cells are present in a culture on a synthetic polymer layer 20 includes comparing morphology of hESCs cultured on the synthetic polymer layer 20 to hESCs cultured on a surface known to allow undifferentiated hESC growth, such as MATRIGEL™. One example of a stain suitable for comparing morphology is precipitated alkaline phosphatase substrate, BCIP/NPT (5-Bromo-4-chloro-3-indolyl phosphate (BCIP)/Nitroblue tetrazolium (NBT). After fixing cells, they may be stained with BCIP/NPT, and morphology can be compared.

In the following, non-limiting examples are presented, which describe various embodiments of the articles and methods discussed above.

EXAMPLES

Example 1

Mild UV Curing and Cyclic Olefin Substrate Increases Layer Uniformity and Decreases Toxicity Introduction:

In this example, monomers are deposited on treated polymeric substrates and are polymerized to obtain uniform coating with little or no cytotoxicity. The coating substrates are cell culture vessels made of polymers, which are suitable for cell culture and stable when contacted with coating monomers. The substrate surfaces were vacuum plasma treated with oxygen to promote monomer spreading. (Meth)acrylate homopolymers and copolymers were employed to produce a synthetic polymeric coating layer on a surface of the culture vessel. The monomers were cured under the protection of inert gas to prevent oxygen-inhibition. The uniformity of the synthetic polymer layer and the cytotoxicity of the resultant layer were examined.

Figure 5A:
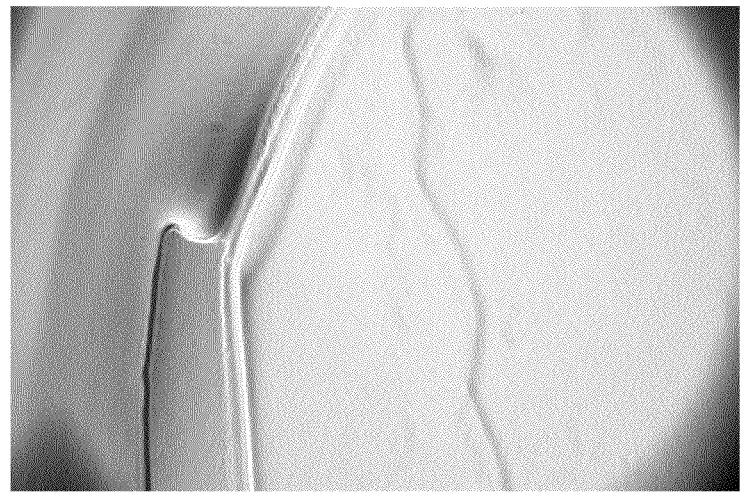
FIGS. 5A-B are phase contrast images of tetra(ethylene glycol) diacrylate cured on wells of tissue culture treated (TCT) polystyrene 96 well cell culture plates using a Fusion UV conveyor belt system (A) and a Xenon pulsed UV system (B).

Materials, Methods and Results:

A layer of homopolymer of tetra(ethylene glycol) diacrylate was coated on Tissue Culture Treated (TCT) polystyrene (Corning, Inc.). Briefly, Tetra(ethylene glycol) diacrylate (Sigma-Aldrich Inc.) was first mixed with 1% (w/w) of photoinitiator Irgacure 819 (Ciba Specialty Chemicals, Inc.). Then 5 µl of the prepared formulation (monomer with photoinitiator) was deposited into each well of TCT treated 96-well polystyrene plate using Matrix® multi-channel pipetter. The plate was allowed to lay horizontally flat for 30 min for the formulation to spread out. The coatings were cured with three passages of total 1.4 J/cm$^2$ using convert belt Fusion UV conveyor belt curing system (belt speed 10 m/min, with N$_2$ blowing). A photograph of a resulting layer is shown in FIG. 5A.

Figure 5B:
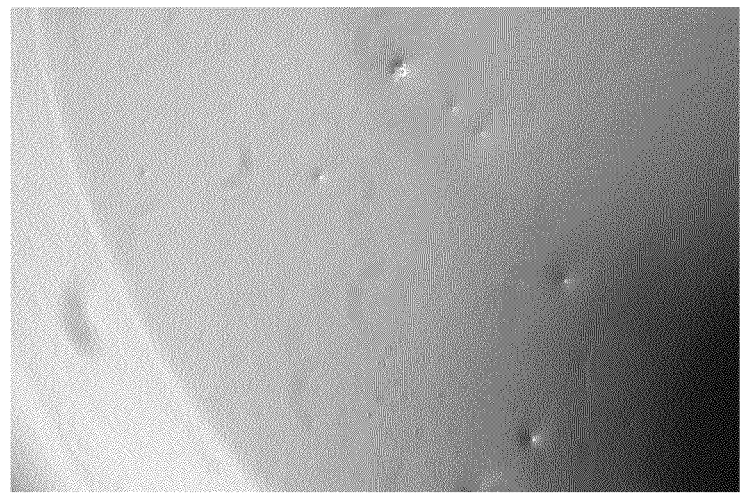
Figure 6A:
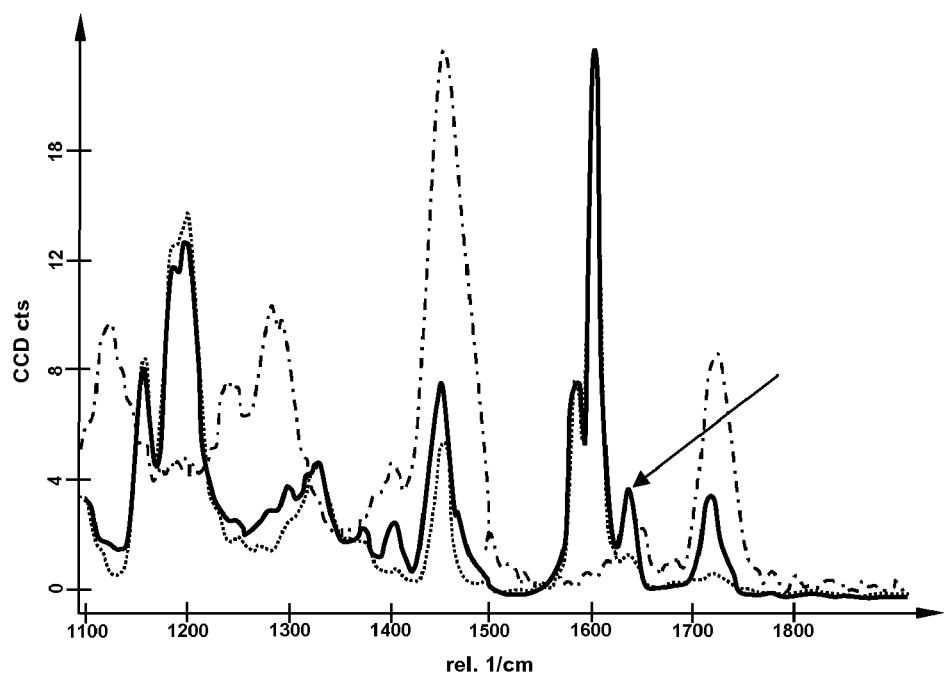
FIG. 6A is a Confocal Raman Microscopy image of a cross section of (meth)acrylic coating (Tri(ethylene glycol) dimethacrylate) on a polystyrene substrate and a corresponding Raman spectra of the substrate and coating polymers.
Figure 6B:
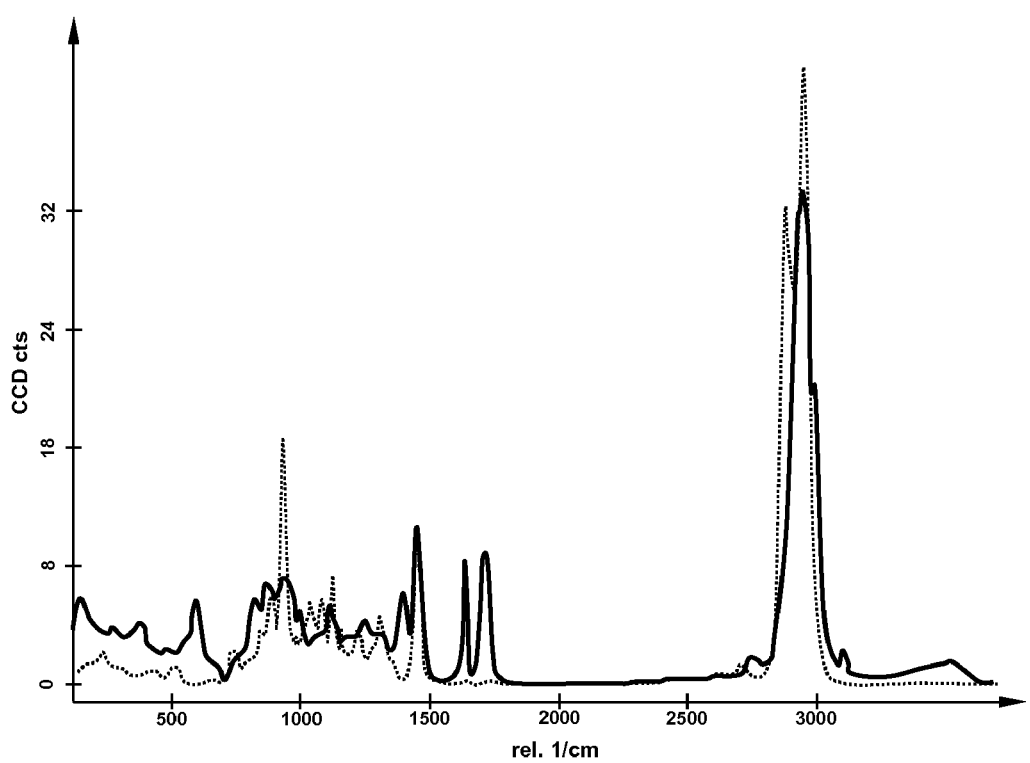
FIG. 6B is a Confocal Raman Microscopy image of a cross section of (meth)acrylic coating (Tri(ethylene glycol) dimethacrylate) on a cyclic olefin copolymer substrate and a corresponding Raman spectra of the substrate and coating polymers.

A layer of homopolymer of tetra(ethylene glycol) diacrylate was coated on TCT polystyrene. Briefly, Tetra(ethylene glycol) diacrylate was first mixed with 1% (w/w) of photoinitiator Irgacure 819. Then 5 µl of the prepared formulation (monomer with photoinitiator) was deposited into each well of TCT treated 96-well polystyrene plate using a Matrix® multi-channel pipetter. The plate was allowed to lay horizontally flat for 30 min for the formulation to spread out. The coatings were cured with 13 mW/cm$^2$ pulsed (100 Hz) UV light (Xenon RC-700) for 1 min in N$_2$ purged box (with fused silica window). A photograph of a resulting layer is shown in FIG. 5B. To compare stability of polystyrene substrate vs. cyclic olefin copolymer, A layer of homopolymer of Tri(ethylene glycol) dimethacrylate was coated on TCT treated polystyrene and vacuum plasma treated cyclic olefin copolymer (TOPAS®) substrates. Briefly, cyclic olefin copolymer substrates were treated using MARCH PLASMOD (March Instruments, Inc) at 0.4 torr O$_2$, 50 watt for 1 min. Tri(ethylene glycol) dimethacrylate (Sartomer Company, Inc.) was first mixed with 1% (w/w) of photoinitiator Irgacure 819. Then the formulation (monomer with photoinitiator) was deposited on TCT treated polystyrene and vacuum plasma treated cyclic olefin copolymer (TOPAS®) substrate to form coatings. The coatings were later cured with 13 mW/cm$^2$ pulsed (100 Hz) UV light (Xenon) for 1 min in N$_2$ purged box (with fused silica window). Confocal Raman Microscope (WiTec Wissenschaftliche Instrumente und Technololgie GmbH, CRM 200) was used to obtain spectral image of cross section of the coating without cutting the samples. FIGS. 6A and 6B are the corresponding spectral images of the coatings on polystyrene and cyclic olefin copolymer respectively. In FIG. 6A, the spectra obtained from the surface (spectra in black, arrow) is a combination of peaks that represent both the polystyrene substrate and the polymer coating (spectra of pure controls in grey). This indicates that the monomer dissolves the polystyrene substrate before polymerization. Hence visualization of the surface spectral images show no clear boundary between the coating and substrate. In FIG. 6B, spectra was obtained at different depths on the surface and were found to be identical to the controls of poly Tri(ethylene glycol) dimethacrylate and cyclic olefin substrate. Visualization of these spectra show a clear boundary between coating and the cyclic olefin substrate suggesting that the substrate is resistant to dissolution by the monomer.

For cytotoxicity studies, coatings of five different (meth) acrylic photopolymers, which were cured using UV Fusion UV system, were prepared as below. Briefly, five different monomers: Tetra(ethylene glycol) diacrylate (TEGDA) (Sigma-Aldrich, Inc.); Glycerol dimethacrylate (GDM) (Sigma-Aldrich, Inc.); Triethylene glycol dimethacrylate (TriEGDM) (Sartomer Company, Inc.); 1,4-Butanediol dimethacrylate (BDM) (Sigma-Aldrich, Inc.); and Poly(ethylene glycol) diacrylate, M$_n$~258 (PEGDA) (Sigma-Aldrich, Inc.), were first mixed with 1% (w/w) of photoinitiator Irgacure 819. Then 5 µl of formulation (monomer with photoinitiator) was deposited into the each well of TCT treated 96-well polystyrene plate using the Matrix® multi-channel pipetter. Each formulation was coating in 6 replicate wells in one plate. The plate was allowed to lay horizontally flat for 30 min for the formulation to spread out. The coatings were cured with three passages of total 1.4 J/cm$^2$ using convert belt Fusion UV curing system (belt speed 10 m/min, with N$_2$ blowing).

For cytotoxicity studies, coatings of five different (meth) acrylic homopolymers, which were cured using Xenon pulsed UV system, were prepared as below. Briefly, five different monomers: Tetra(ethylene glycol) diacrylate (TEGDA); Glycerol dimethacrylate (GDM); Triethylene glycol dimethacrylate (TriEGDM); 1,4-Butanediol dimethacrylate (BDM); and Poly(ethylene glycol) diacrylate MW~258 (PEGDA), were first mixed with 1% (w/w) of photoinitiator Irgacure 819. Then 5 µl of formulation (monomer with photoinitiator) was deposited into the each well of plasma treated 96-well cyclic olefin plates using Matrix® multi-channel pipetter. 96-well cyclic olefin plates were provided by Corning Life Science internal development group. Before coating, cyclic olefin copolymer plates were treated using MARCH PLASMOD (March Instruments, Inc) at 0.4 torr O$_2$, 50 watt for 1 min. Each formulation was coating in 6 replicate wells in one plate. The plate was allowed to lay horizontally flat for 30 min for the formulation to spread out. The coatings were cured with 13 mW/cm$^2$ pulsed (100 Hz) UV light (Xenon RC-700) for 1 min in N$_2$ purged box (with fused silica window).

All 96-well plates were sterilized by 25-35 kGy Gamma radiation prior to cell cytotoxicity analysis. Human lung fibroblasts (MRC5, ATCC# CCL-171) were grown to confluency in Iscove's Modified Dulbecco's Medium supplemented with 10% fetal bovine serum at standard cell culture conditions. Cells were harvested using 0.05% trypsin/EDTA and seeded at a density of 15,000 cells/well. Cells were grown at standard cell culture conditions (5% CO$_2$, 37° C.). The CellTiter 96® AQueous One Solution Cell Proliferation Assay (G3581, Promega Corporation) was used to determine the relative number of viable cells on each surface after 72 hours in culture. The assay was performed according to the manufacturer's protocol. Briefly, after aspiration of culture media, a 1:5 dilution of MTS tetrazolium reagent in phosphate buffered saline was added directly to cells. After 1 hour of incubation at 37° C. and 5% CO$_2$, the absorbance at 490 nm was recorded. Corning Ultra Low Attachment (ULA®) and uncoated TCT surface were used as negative and positive control surfaces, respectively. This data was used to determine (meth)acrylic formulation cytotoxicity. As shown in FIG. 7, the Fusion UV curing process resulted in a highly cytotoxic layer, while the coating prepared using the Xenon pulsed UV curing system had similar cell viability as the positive control of commercially available TCT-treated polystyrene surfaces.

Figure 7A:
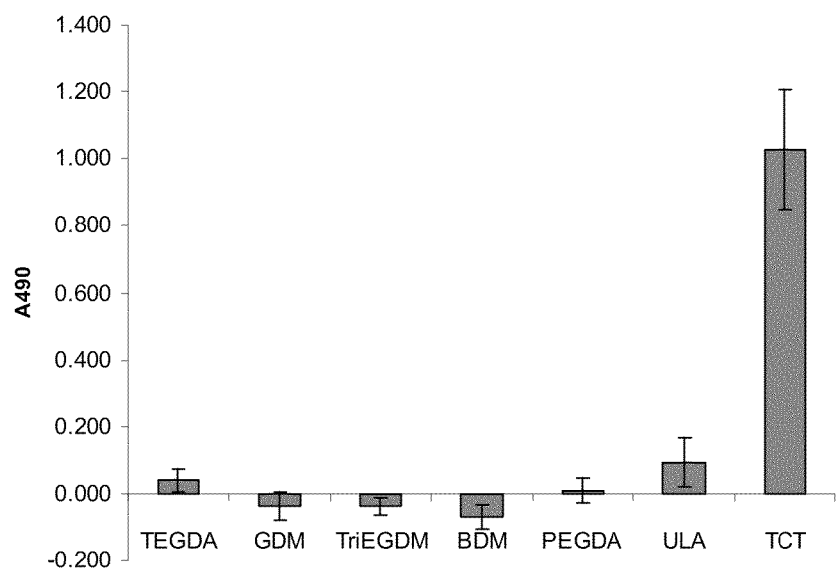
FIGS. 7A-B are bar graphs showing results of a MRC5 cell proliferation (CellTiter, Promega) assay of synthetic polymer layers formed on substrates using different UV curing parameters; Fusion UV conveyor belt system (A) and Xenon pulsed UV system (B).
Figure 7B:
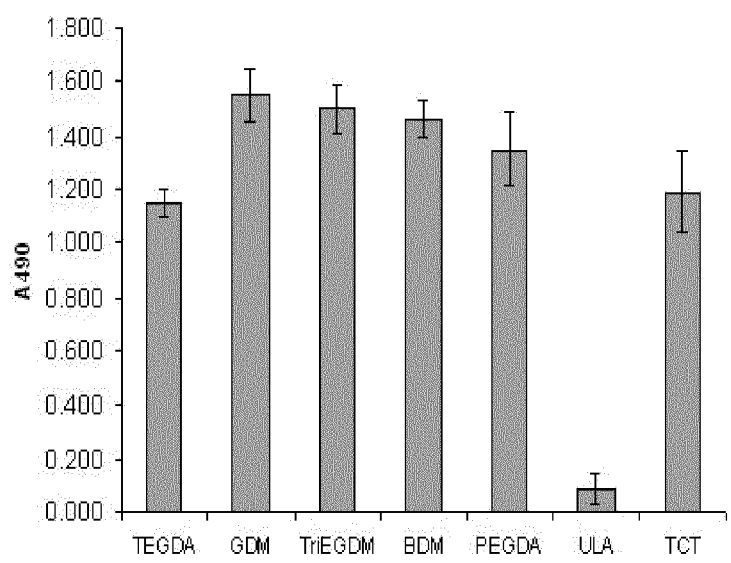

Discussion:

To cure (meth)acrylate monomers, a high power of UV light is usually believed beneficial for a higher conversion of the polymerization (Decker, C. (1998). "The use of UV irradiation in polymerization." Polymer International 45(2): 133-141). However, when monomer coatings were cured along with high density UV light on another polymer surface, they were found to have low uniformity (FIGS. 5A and 5B) and high cytotoxicity due to uncontrolled polymerization and low molecular weight fragments from incomplete curing (FIGS. 7A and 7B). This issue significantly interferes with cell attachment and proliferation.

Polystyrene, which has been used broadly in cell culture ware, can be dissolved by many monomers, which will affect the polymer coating properties and reliability of the cell screening results on corresponding coatings. In comparison, the cyclic olefin substrate was found to be more stable after contact with a variety of monomers. In all the monomers tested, no interaction between monomer formulation and substrate was observed. Cyclic olefin copolymer also has very good UV permeability and has been used broadly as container for pharmaceutical products. Therefore, in embodiments of the present invention, it should provide a suitable material for polymer coating processes and different cell screening assays.

The data presented herein shows that pulsed UV curing with suitable power and length of exposure provides a uniform coating with no significant cytotoxicity for cell culture. The curing process also reduced the heat during polymerization, which is important for thermoplastic polymeric substrates. This coating and curing process can be applied to a variety of photopolymerizable monomers. Therefore it is possible to provide diversified materials properties from a large variety of monomers to meet the needs of different cell culture and biomedical applications.

Conclusion:

Pulsed or continuous UV light systems with suitable power and length of exposure can be used to cure the coating. This reduces heat to which many polymer substrates are sensitive. It also provides better control over curing kinetics, higher conversion and lower shrinkage to provide more uniform and less toxic coated surfaces. The curing may occur under nitrogen protection to prevent oxygen inhibition and further increase polymer conversion. It was found that both conditions together (controlled UV and nitrogen protection) reduce the cytotoxicity of obtained (meth)acrylic coatings.

The higher conversion may allow for elimination of an extra washing step, which can simplify the manufacturing process and reduce waste generation during the washing process.

Cyclic olefin can provide a suitable cell culture vessel as the coating substrate. It is stable when exposed to a variety of monomers and suitable for a variety of UV-fluorescence bioassays, as well as UV curing.

The selected curing process is not sensitive to monomer structure. This provides a platform to effectively create diversified biomaterial coatings for different cell culture applications.

Example 2

High Throughput Screening Photopolymer Process for Cell Culture

This example provides the basis for a highly efficient solvent-based process for generating synthetic polymer surfaces from a large diversity of monomers that is applicable to large area cell culture wares.

Figure 8A:
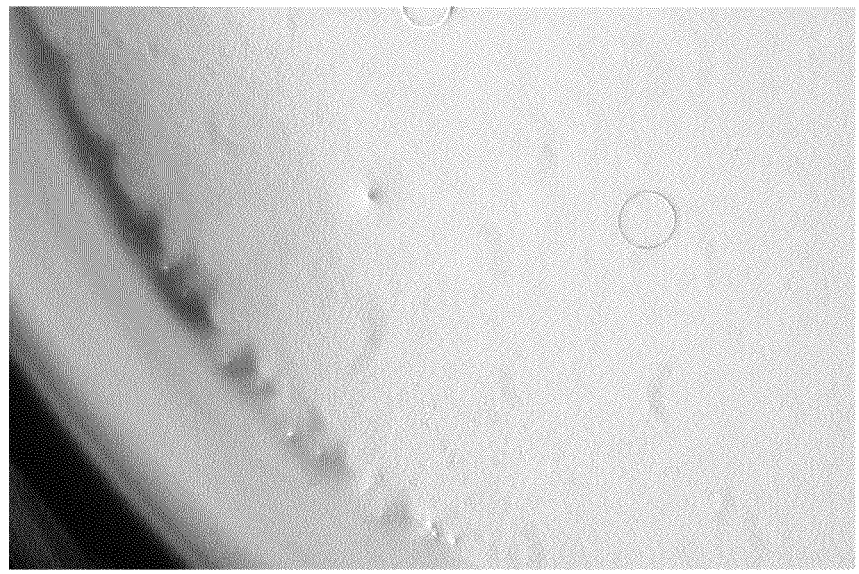
FIGS. 8A-B are phase contrast images of (meth)acrylic coating polymerized from tetra(ethylene glycol) diacrylate using a 1/1 (A) or 9/1 (B) ethanol/monomer process.

Materials, Methods, and Results:

A layer of homopolymer of tetra(ethylene glycol) diacrylate was coated in a 96-well cyclic olefin copolymer plate using different ethanol processes. Briefly, Tetra(ethylene glycol) diacrylate (Sigma-Aldrich, Inc) was first mixed with 1% w/v (photoinitiator/monomer) of photoinitiator Irgacure 819 (Ciba Specialty Chemicals, Inc.) and 1/1 or 9/1 (ethanol[volume]/monomer[volume]) of ethanol depending on experimental design. Then 5 µl of the prepared formulation (monomer, photoinitiator and ethanol) was deposited in each well of plasma treated 96-well cyclic olefin copolymer plate using BioTek Precision Microplate Pipetting System. The formulation solutions spread immediately and the plate was allowed to lay horizontally flat for 3 hr in fume hood for the ethanol to evaporate. This allowed >99% of ethanol to be removed. The coatings were then cured with 13 mW/cm² pulsed (100 Hz) UV light (Xenon RC-801) for 1 min in $N_2$ purged box (with fused silica window). Phase contrast photographs of the edge of resulting layers are shown in FIG. 8A (from 1/1 ethanol process) FIG. 8B (from 9/1 ethanol process). Thick coating (from 1/1 ethanol process) leads to accumulation of monomer formulation at the periphery of the well due to meniscus effect from surface tension of formulation. Thin coating (from 9/1 ethanol process) created more even coating (without meniscus effect) across the well. Contact angle also confirmed that with both processes, the wells were completely covered with designed (meth)acrylic coating.

A layer of homopolymer of Glycerol 1,3-diglycerolate diacrylate was coated in a 96-well cyclic olefin copolymer plate with 1/1 or 9/1 ethanol process as described above.

Figure 9A:
FIGS. 9A-B are phase contrast images of (meth)acrylic coating polymerized from Glycerol 1,3-diglycerolate diacrylate using a 1/1 (A) or 9/1 (B) ethanol/monomer process.
Figure 9B:

After curing, 200 µl of water was added in each well of the plate and then the plate was incubated at 37° C. over night. Finally the water was removed and phase contrast images of the coating layer were taken. Phase contrast photographs of the center of resulting layers are shown in FIG. 9A (from 1/1 ethanol process) FIG. 9B (from 9/1 ethanol process). Wrinkles in thick coating (using concentrated 1/1 ethanol process) as shown in FIG. 9A suggest de-lamination after contact with aqueous medium. While no de-lamination was observed in thin coating from diluted 9/1 ethanol process as shown in FIG. 9B.

The cytotoxicity of (meth)acrylic surfaces in 96-well format produced by an ethanol process was determined. Briefly, copolymers from the blends of two different monomers were prepared as the homopolymer described above. The monomers are shown in Table 3. Three volume ratios of 90:10, 70:30, and 50:50 of each combination of majority and minority components was blended and mixed with 1% w/v (photoinitiator/total monomers) of photoinitiator Irgacure 819 and 9/1 (v/v) ethanol. Then 5 µl of the prepared formulation (monomer, photoinitiator and ethanol) was deposited in each well of plasma treated 96-well cyclic olefin copolymer plate using BioTek Precision Microplate Pipetting System. The formulation solutions spread immediately and the plate was allowed to lay horizontally flat for 3 hr in fume hood for the ethanol to evaporate. The coatings were then cured with 13 mW/cm² pulsed (100 Hz) UV light (Xenon RC-801) for 1 min in $N_2$ purged box (with fused silica window). After curing, a washing step was taken. Briefly, the surface in each well of 96-well plates was incubated with 200 µL of >99% ethanol for 1 hr followed by 200 µL of water for over night to remove potential extractables. Finally the surfaces were air dried before sterilization.

TABLE 3

Formulation compositions

| Formulation ID | Majority Monomer | Minority Monomer |
|---|---|---|
| 48-3 | 1,6-Hexanediol propoxylate diacrylate | Trimethylolpropane ethoxylate (1 EO/OH) methyl |
| 48-5 | 1,6-Hexanediol propoxylate diacrylate | 1,6-Hexanediol ethoxylate diacrylate |
| 53-3 | Neopentyl glycol dimethacrylate | Triethylene glycol dimethacrylate |
| 53-4 | Neopentyl glycol dimethacrylate | 1,4-Butanediol dimethacrylate |

TABLE 3-continued

Formulation compositions

| Formulation ID | Majority Monomer | Minority Monomer |
|---|---|---|
| 53-7 | Trimethylolpropane benzoate diacrylate | Glycerol dimethacrylate |
| 53-9 | Trimethylolpropane benzoate diacrylate | 1,4-Butanediol dimethacrylate |
| 53-10 | Trimethylolpropane benzoate diacrylate | Poly(ethylene glycol) diacrylate |
| 55-3 | 1,6-Hexanediol ethoxylate diacrylate | Triethylene glycol dimethacrylate |

Figure 10:
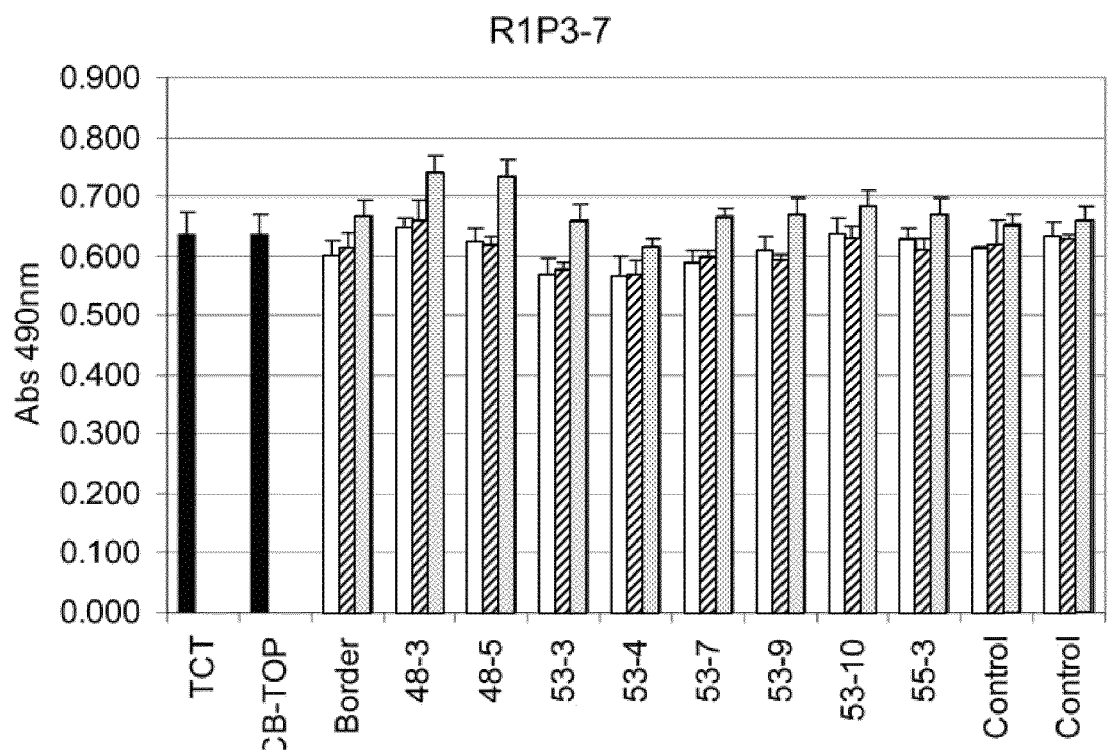
FIG. 10 is a bar graph showing results of a MRC5 cell proliferation (CellTiter, Promega) assay of (meth)acrylic surfaces using an ethanol process. The coatings were polymerized from blends of two different monomers with majority and minority components of 50:50, 70:30, and 90:10, respectively.

All 96-well plates were sterilized by 25-35 kGy Gamma radiation prior to cell cytotoxicity analysis. Human lung fibroblasts (MRC5, ATCC# CCL-171) were grown to confluency in Iscove's Modified Dulbecco's Medium supplemented with 10% fetal bovine serum at standard cell culture conditions. Cells were harvested using 0.05% trypsin/EDTA and seeded at a density of 15,000 cells/well. Cells were grown at standard cell culture conditions (5% $CO_2$, 37° C.). The CellTiter 96® AQueous One Solution Cell Proliferation Assay (G3581, Promega Corporation) was used to determine the relative number of viable cells on each surface after 72 hours in culture. The assay was performed according to the manufacturer's protocol. Briefly, after aspiration of culture media, a 1:5 dilution of MTS tetrazolium reagent in phosphate buffered saline was added directly to cells. After 1 hour of incubation at 37° C. and 5% $CO_2$, the absorbance at 490 nm was recorded. This data was used to determine (meth)acrylic formulation cytotoxicity, as shown in FIG. 10.

The cytotoxicity of (meth)acrylic surfaces in 6-well format produced by an ethanol process was determined. Plasma treated cyclic olefin copolymer plates (6-well) were used. Homopolymers and copolymers from the blends of two different monomers were prepared as described above. Monomer compositions of those polymers are listed below. 1. Glycerol dimethacrylate; 2. Triethylene glycol dimethacrylate; 3. 1,4-Butanediol dimethacrylate; 4. Poly(ethylene glycol) diacrylate; 5. Triethylene glycol dimethacrylate (70%), Glycerol dimethacrylate (30%); 6. Tetra(ethylene glycol) diacrylate (70%), Glycerol dimethacrylate (30%). For all the formulations, a ratio of 1/0.01/9 of monomer[volume]/photoinitiator [weight]/ethanol[volume] was prepared. 80 µl of the formulation was added in each well. The formulation started to spread out in 1 min and the plate was allowed to lay horizontally flat for 3 hr in fume hood for the ethanol to evaporate. This allowed >99% of ethanol to be removed. The coatings were then cured with 13 mW/cm² pulsed (100 Hz) UV light (Xenon RC-801) for 1 min in $N_2$ purged box (with fused silica window). After curing, a washing step was taken. Briefly, the surface in each well of 6-well plates was incubated with 4 mL of >99% ethanol for 1 hr followed by 4 mL of water over night to remove potential extractables. Finally the surfaces were air dried before sterilization.

Figure 11A:
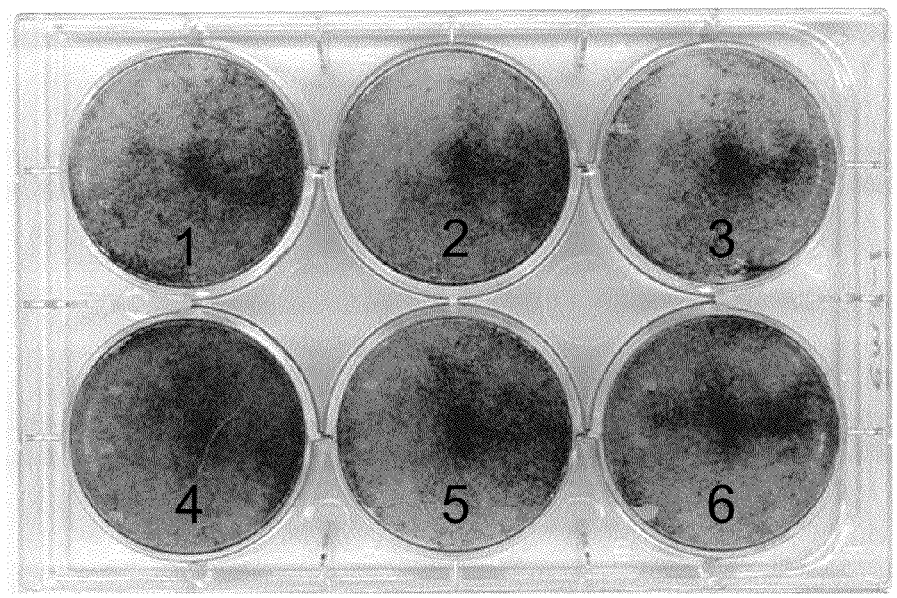
FIGS. 11A-B are images of crystal violet stained MRC5 cells adhered to (meth)acrylate surfaces. (A) 6-well plate coated with (meth)acrylic polymers. Monomer compositions of the (meth)acrylic polymers are (1) Glycerol dimethacrylate; (2) Triethylene glycol dimethacrylate; (3) 1,4-Butanediol dimethacrylate; (4) Poly(ethylene glycol) diacrylate; (5) Triethylene glycol dimethacrylate (70%), Glycerol dimethacrylate (30%); (6) Tetra(ethylene glycol) diacrylate (70%), Glycerol dimethacrylate (30%). (B) TCT control surfaces.
Figure 11B:
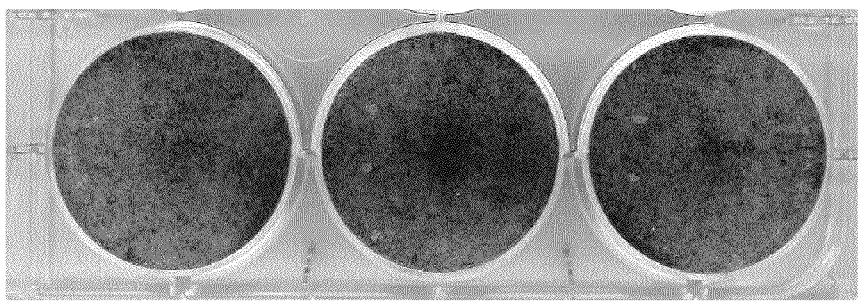

All 6-well plates were sterilized by 25-35 kGy Gamma radiation prior to cell cytotoxicity analysis. Human lung fibroblasts (MRC5, ATCC# CCL-171) were grown to confluency in Iscove's Modified Dulbecco's Medium supplemented with 10% fetal bovine serum at standard cell culture conditions. Cells were harvested using 0.05% trypsin/EDTA and seeded at a density of 100,000 cells/well. Cells were grown at standard cell culture conditions (5% $CO_2$, 37° C.). The CellTiter 96® AQueous One Solution Cell Proliferation Assay (G3581, Promega Corporation) was used to determine the relative number of viable cells on each surface after 72 hours in culture. The assay was performed according to the manufacturer's protocol. Briefly, after aspiration of culture media, a 1:5 dilution of MTS tetrazolium reagent in phosphate buffered saline was added directly to cells. After 1 hour of incubation at 37° C. and 5% $CO_2$, the absorbance at 490 nm was recorded. All (meth)acrylic surfaces in 6-well format were found to be non-toxic via the CellTiter assay. Further, to better visualize any changes in cell morphology or uniform cell attachment, MTS reagent was aspirated from wells, and 1 mL of a 1:5 dilution of crystal violet stain in water was added. After staining for 5 minutes, each well was washed 3 times with water. Plates were allowed to dry and a representative photo was taken as shown in FIGS. 11A-B. FIGS. 11A-B: Crystal violet assay of (meth)acrylic surfaces in 6-well format vs. TCT treated control surface. No interference in cell spreading or morphology was noted on (meth)acrylic coating surfaces vs. TCT control.

Discussion:

Highly viscous monomers can make automated liquid handling difficult during formulation or coating. High viscosity also prevents spreading of monomer during the coating process. These issues potentially prevent the high throughput material screening of thin uniform coatings for large area cell culture ware. A solution to these issues is the introduction of a solvent. However normal solvents for most polymers are usually toxic to cells and may be difficult to remove. Given that our substrate is a polymer, it could be dissolved in solvent during coating process as well. In this Example we used ethanol as solvent for monomers during formulation and coating. Then ethanol was removed before the curing process. This also reduced monomer consumption due to thinner coating, which makes it more efficient for large materials library screening.

This method improves formulation efficiency. Before this method, a 576-formulation library of binary blends from 24 monomers, would have been made based on weight. The entire process could take 40-50 hours/person. By using ethanol in the process, the blending can be made by using liquid handling instrument based on volume. The same 576 formulations may be formulated in about 4 hours/person—a 10-fold improvement in efficiency.

This method improves coating efficiency. Ethanol reduces monomer viscosity and promotes monomer spreading during the coating process. This enables the application of automated instrumentation in the coating process as well. Using the ethanol process, a library of 512 different surfaces can be coated in 96-well microplates in 2-3 hours vs. 50+ hours by using monomer only. Application of ethanol in coating further enhances high throughput in the screening system.

Figure 8B:

This method also improves coating uniformity and reduces possible coating de-lamination. Previous experiments showed that monomer viscosity is the major factor which determines monomer formulation spreading during coating process. Therefore a larger volume of monomers had to be coated on the same surface area which leads to thicker coating. For example, without solvent the coating was about 20-50 µm. Thick coating was found to be the cause of increased non-uniformity due to the meniscus effect, as shown in FIG. 8A and de-lamination after contact with aqueous solution or cell culture medium, as shown in FIG. 9A. In addition, manual spreading was often necessary to ensure full surface coverage. By using ethanol, formulations are less viscous and spread immediately. By reducing the concentration of monomer in ethanol less monomer can be used to cover the same amount of surface area. The coating thickness was found in the range of <10 µm. Coating uniformity and de-lamination issues can be significantly improved, as shown in FIG. 8B and FIG. 9B.

Acrylic surfaces with a diversity of chemical structures created using this method were also evaluated for cytotoxicity in a cell viability assay over 72 hours and were found non-toxic (FIG. 10, graph). In addition, no interference in cell spreading or morphology (via crystal violet staining) was noted (FIG. 11 plates images). Further, this ethanol process maintains (meth)acrylic-coating consistency in larger 6-well plate formats with uniform cell spreading and proliferation.

Ethanol brings several benefits to the process. (1) It reduces monomer viscosity, makes it possible to use automated instrumentation in the formulation process and increases efficiency up to 10 times. This makes it possible to do high throughput material screening. (2) It promotes monomer spreading to achieve a thin and uniform coating for small or large surface areas using automated liquid handling instrumentation and increases coating efficiency. (3) It reduces the amount of monomer to be used for the coating process and the final coating thickness. This can reduce cost by reducing consumption of monomers while reducing stress in coating during polymerization and swelling after contact with culture medium and finally reduces coating de-lamination.

Compared to other solvents, ethanol can also provide additional benefits: (1) ethanol is used for biomedical or pharmaceutical processes and thus should be safe for the manufacture of cell culture ware for therapeutic cells or tissues; (2) it is commercially available in USP grade; (3) it is easy to evaporate and may be removed after the coating process without extreme conditions such as vacuum or heat; (4) there is minimal concern for waste management or safety protection; (5) it is a good solvent for a large majority of (meth)acrylic monomers but is a poor solvent for most polymers used in cell culture ware as a substrate; and (6) it can be readily removed before curing and is inert during free radical polymerization, and thus side affects on the subsequent polymerization of the coating should be minimal.

Example 3

Human Embryonic Stem Cell Screening

Materials and Methods:

Acrylate surfaces prepared using ethanol as a solvent have been screened for human embryonic stem cell attachment and growth. Briefly, the majority and minority monomers as shown in Table 4 were blended according to the volume ratios of 70:30 and mixed with 1% w/v (photoinitiator/total monomers) of photoinitiator Irgacure 819 and 9/1 (ethanol[volume]/total monomer[volume]) of ethanol. Then 5 µl of the prepared formulation (monomer, photoinitiator and ethanol) was deposited in each well of plasma treated 96-well cyclic olefin copolymer plate using BioTek® Precision Microplate Pipetting System. The formulation spread immediately and the plate was allowed horizontal flat in fume hood for 3 hr for the ethanol to evaporate. The coatings were then cured with 13 mW/cm$^2$ pulsed (100 Hz) UV light (Xenon RC-801) for 1 min in N$_2$ purged box (with fused silica window). After curing, a washing step was performed. Briefly, the surface in each well of 96-well plates was incubated with 200 µL of >99% ethanol for 1 hr followed by 200 µL of water overnight to remove potential extractables. Finally the surfaces were air dried before sterilization.

TABLE 4

Formulation compositions

| Formulation ID | Majority Monomer | Minority Monomer |
|---|---|---|
| 22-1 | Glycerol dimethacrylate | Di(ethylene glycol) dimethacrylate |
| 24-5 | Tetra(ethylene glycol) diacrylate | 1,6-Hexanediol ethoxylate diacrylate, M$_n$ ~314 |
| 27-1 | Tetra(ethylene glycol) diacrylate | Neopentyl glycol ethoxylate diacrylate |
| 53-3 | Neopentyl glycol dimethacrylate | Triethylene glycol dimethacrylate |
| 53-4 | Neopentyl glycol dimethacrylate | 1,4-Butanediol dimethacrylate |
| 53-7 | Trimethylolpropane benzoate diacrylate | Glycerol dimethacrylate |
| 53-9 | Trimethylolpropane benzoate diacrylate | 1,4-Butanediol dimethacrylate |
| 53-10 | Trimethylolpropane benzoate diacrylate | Poly(ethylene glycol) diacrylate |

All 96-well plates were sterilized by 25-35 kGy Gamma radiation prior to cell culture. MATRIGEL™ coated wells were used as positive control. H1 hES cells (Geron Corporation) were cultured according to Geron's protocols. Briefly, cells were cultured on MATRIGEL™-coated TCT flasks or 6-well plates in chemically defined medium (X-Vivo10 basal medium supplemented with human recombinant growth factors, available from Geron Corp.). Cells were passaged every 5 days at the seeding density of 0.5-1×10$^6$ cells/well of 6-well plate (~50,000-100,000 cell/cm$^2$) using Geron's sub-cultivation procedure (collagenase IV, followed by washing with DPBS, scraping and re-suspending in chemically defined culture medium).

For the experiments, cells were seeded at the density of 35,000/well of 96-well plate (116,000 cells/cm$^2$) on the experimental surfaces or on MATRIGEL™-coated wells as positive control using MultidropCombi (ThermoFisher) automated dispenser. Cells were cultured for 48 hrs under standard cell culture conditions (37° C. with 5% CO$_2$) and processed for AttoPhos assay as described below.

AttoPhos quantitative assay was used to examine the number of alkaline phosphatase-positive (undifferentiated) colonies within each well. Alkaline phosphatase (AP) is a marker for undifferentiated hES cells. AP expression is lost or significantly reduced as cells differentiate.

At the end of incubation time, cells were rinsed with 150 µl of Dulbecco's phosphate buffered saline (DPBS) and fixed with 4% paraformaldehyde for 10 min at R/T (70 µl/well of 96-well plate). Cells were washed once with 150 µl of DPBS, and treated for 10 min with 100 µl of AttoPhos fluorescent substrate (diluted 1:3 in DPBS) protected from light. AttoPhos fluorescent intensity at 485/535 nm was obtained using Victor 3 microplate reader (Perkin Elmer).

Figure 12:
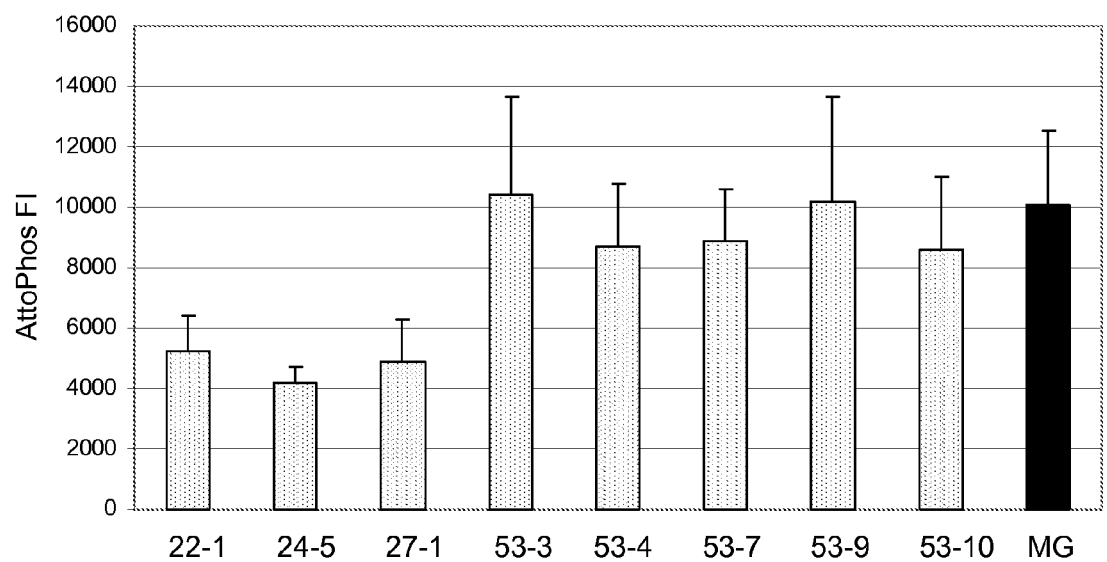
FIG. 12 is a bar graph of results from alkaline phosphatase expression of H1 human embryonic stem cell line on different substrates.

Results and Discussion:

In this Example short-term growth of H1 hES cells was screened on embodiments of different (meth)acrylic surfaces, synthetic polymer surfaces, created using an ethanol coating process. Cells were seeded at the density of 35,000/well into 96 well plates coated with (meth)acrylic polymer or MATRIGEL™, as a positive control using serum-containing media Xvivo10 (with 20% FBS+80 ng/ml bFGF+0.5 ng/ml of TGFβ1. 48 hrs later, cells were fixed and processed for AttoPhos staining as described in Materials and Methods to examine for the presence of undifferentiated (alkaline phosphatase-positive) hES cells. In the serum-containing medium condition, AttoPhos fluorescence for the surfaces 53-3, 53-4, 53-7, 53-9, 53-10, were very similar to MATRIGEL™ control. (FIG. 12). BCIP staining was performed to confirm normal undifferentiated stem cell colony morphology on these surfaces (data not shown). In the absence of a peptide conjugated to the synthetic polymer coating, serum-free media conditions did not support H1 cells (data not shown). These data suggest that surfaces created using an ethanol coating process could be used to screen attachment and short term growth of undifferentiated hES cells in serum-containing media conditions. This in turn can provide a powerful screening platform for surface and medium optimization for hES cell culture.

Example 4

Varying Solvents Result in Suitable Coatings

In the Examples above, we described a solvent process using ethanol which not only enables high throughput coating of a material library for cell culture but also provides access to materials with a range of physical properties extending from a highly crosslinked hard polymer to swellable (meth)acrylate polymers. Using surfaces from the above processes we were able to conjugate bioactive molecules, such as peptides, and for the first time provide a synthetic polymer surface which can support undifferentiated human stem cell culture in chemically defined medium. In this Example, we extended the selection of solvents as listed in Table 5 for testing.

TABLE 5

List of solvents for testing

| Solvent | Bp | Mp | Comments |
| --- | --- | --- | --- |
| Diethyl ether | 34.6 | −116.3 | |
| Acetone | 56.2 | −94.3 | |
| Methanol | 64.6 | −98 | |
| Hexane | 69 | −95 | Low polar solvent control |
| Ethyl acetate | 77 | −83.6 | |
| Ethanol | 78.5 | −114.1 | |
| Butanone | 79.6 | −86.3 | |
| Acetonitrile | 81.6 | −46 | |
| 2-propanol | 82.4 | −88.5 | |
| 2-butanol | 98 | −115 | |
| Water | 100 | 0 | High polar solvent control |
| Dimethyl-formamide | 153 | −61 | |

A series of monomer formulations were also selected to cover a range of monomers which provided a variety of physical properties after polymerization. Formulations for highly crosslinked polymers included TEGDA, GDMA, and BDMA. A formulation for swellable (meth)acrylate polymers was SA02. These formulations are shown in Table 6. Solubility of four formulations in twelve selected solvents are listed in Table 7. The results suggested that hexane and water were not suitable for formulations that will become highly crosslinked (meth)acrylic polymers, while ethyl ether and hexane were not suitable for swellable (meth)acrylate formulations. All the solvents except hexane were also inert with respect to the cyclic olefin copolymer used as the base material for cell culture vessels.

To prepare highly crosslinked polymer coatings, 1 ml of corresponding monomer (TEGDA, GDMA or BDMA) was mixed with 30 µl photoinitiator Irgacure 2022 as stock formulation. Then 250 µl of stock formulation was dissolved into 250 µl of selected solvents from Table 5 to prepare 50% formulation solutions. Due to miscibility issues, hexane and water were not selected for this test. Then 2 µl of 50% formulation solution were deposited into each well of a 96-well cyclic olefin plate. The plates were treated with vacuum plasma before formulation deposition. Specifically, the vacuum plasma treatment was Corning CellBind treatment. Later, the solvents were evaporated in dry environment, such as nitrogen, for 3 hr to remove majority of the solvents and prevent condensation of humidity on the coating surface. Finally, the plates were cured using Xenon 800 pulsed UV curing system for 60 seconds with dose of 10-15 mW/cm$^2$ in nitrogen to prevent oxygen inhibition. All of the formulations in Table 6 contain 30 µl of Irgacure 2022 (80% Darocur 1173, 20% Irgacure 819) as photoinitiator.

TABLE 6

List of tested formulations

| Code | Formulation | Comments |
| --- | --- | --- |
| TEGDA | Tetra(ethylene glycol) diacrylate (1000 µl) | Highly crosslinked hydrophilic acrylate |
| GDMA | Glycerol dimethacrylate (1000 µl) | Highly crosslinked hydrophilic, methacrylate |
| BDMA | 1,4 butandiol dimethacrylate (1000 µl) | Highly crosslinked hydrophobic, methacrylate |
| SA02 | HEMA (800 µl), Carboxyethyl acrylate (200 µl), Tetra(ethylene glycol) dimethacrylate (30 µl) | Loosely crosslinked swellable (meth)acrylate coating |

TABLE 7

Solubility of selected formulations with different solvents.

| Solvent | TEGDA | GDMA | BDMA | SA02 |
| --- | --- | --- | --- | --- |
| Diethyl ether | ✓ | ✓ | ✓ | ○ |
| Acetone | ✓ | ✓ | ✓ | ✓ |
| Methanol | ✓ | ✓ | ✓ | ✓ |
| Hexane | x | x | ✓ | x |
| Ethyl acetate | ✓ | ✓ | ✓ | ✓ |
| Ethanol | ✓ | ✓ | ✓ | ✓ |
| Butanone | ✓ | ✓ | ✓ | ✓ |
| Acetonitrile | ✓ | ✓ | ✓ | ✓ |
| 2-propanol | ✓ | ✓ | ✓ | ✓ |
| 2-butanol | ✓ | ✓ | ✓ | ✓ |
| Water | x | x | x | ✓ |
| DMF | ✓ | ✓ | ✓ | ✓ | x - not soluble at from 1:10 to 1:1 ratio of solvent vs. formulation
✓ - soluble from 1:10 to 100:1 ration of solvent vs. formulation
○ - not soluble at 100:1 ration of solvents vs. formulation.

For purposes of comparison with traditional solution polymerization, 375 µl of stock formulations were also dissolved in 125 µl of DMF to obtain 75:25 formulation solutions. Then 2 µl of formulation solution was deposited into each well of 96-well cyclic olefin plates. The plates had been treated with CellBind treatment-vacuum plasma treatment as described above. Without allowing for solvent evaporation, the plates were cured immediately using Xenon RC-800 pulsed UV curing system for 60 seconds with dose of 10-15 mW/cm$^2$ in nitrogen environment to prevent oxygen inhibition to free radical polymerization.

To evaluate extractables from selected coating and processes, 200 µl of ethanol was filled in each well followed by shaking the plates at room temperature for 1 hr before collecting the ethanol for HPLC analysis. The HPLC system consisted of a Waters Alliance 2695 Chromatography system equipped with a 96 Waters Photodiode Array Detector and a Nova Pak C18 (4µ) column. The flow rate was 1 mL/min. A gradient flow of acetonitrile and water was used. The gradient started at 95/05 water/acetonitrile and progressed to 0/100 water/acetonitrile over 45 minutes. The column temperature was maintained at 35° C. All data were analyzed at 215 nm.

The final results were list Table 8. In all the tested solvents only DMF can be detected either from bulk or solution polymerization method, particularly in solution polymerization. Extra steps, such as extensive washing or long vacuum time, may be needed with such solution polymerization methods or DMF to remove the solvent. In contrast, using other solvents with relatively low boiling point, such as diethyl ether, acetone, methanol, ethyl acetate, ethanol, butanone, acetonitrile, 2-propanol, 2-butanol, residual solvent should not be a concern.

TABLE 8

| Solvent | Formulation | | |
|---|---|---|---|
| | TEGDA | GDMA | BDMA |
| | Solvent Extractables (%) | | |
| Diethyl ether | No | No | No |
| Acetone | No | No | No |
| Methanol | No | No | No |
| Ethanol | No | No | No |
| 2-Butanol | No | No | No |
| DMF | 0.0004 | 0.0060 | 0.0012 |
| 25% DMF | 0.0140 | 0.1200 | 0.0330 |

Figure 13:
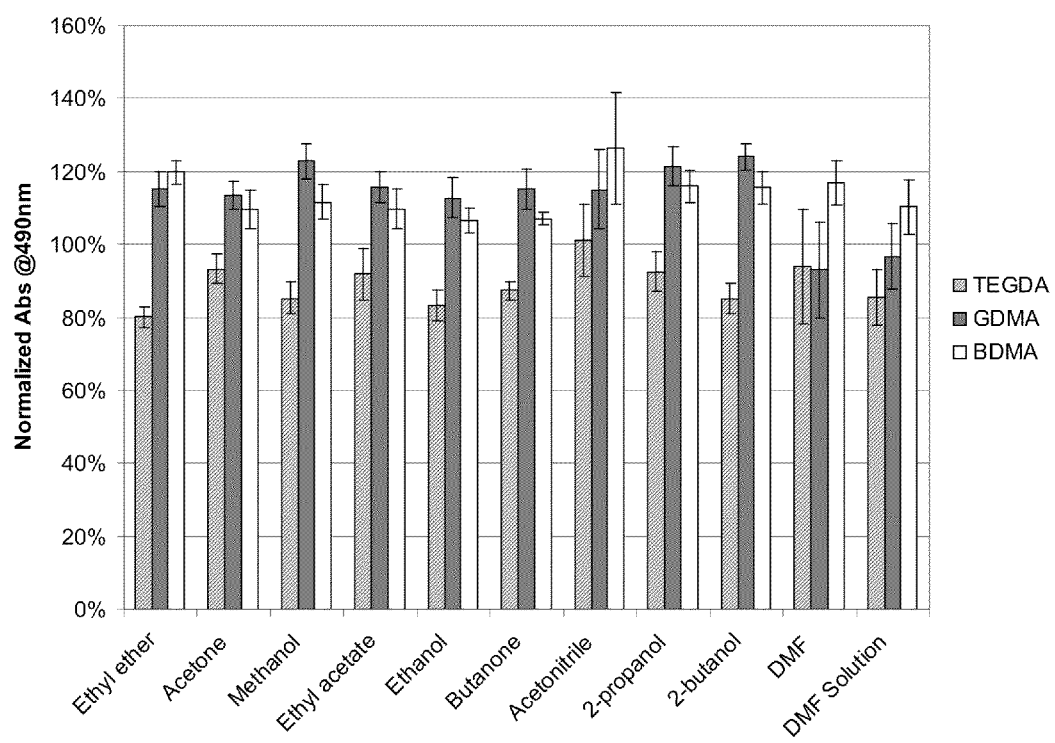
FIG. 13 is a bar graph showing results of a MRC5 cell proliferation assay on polymer layers coated using different solvents.
Figure 14:
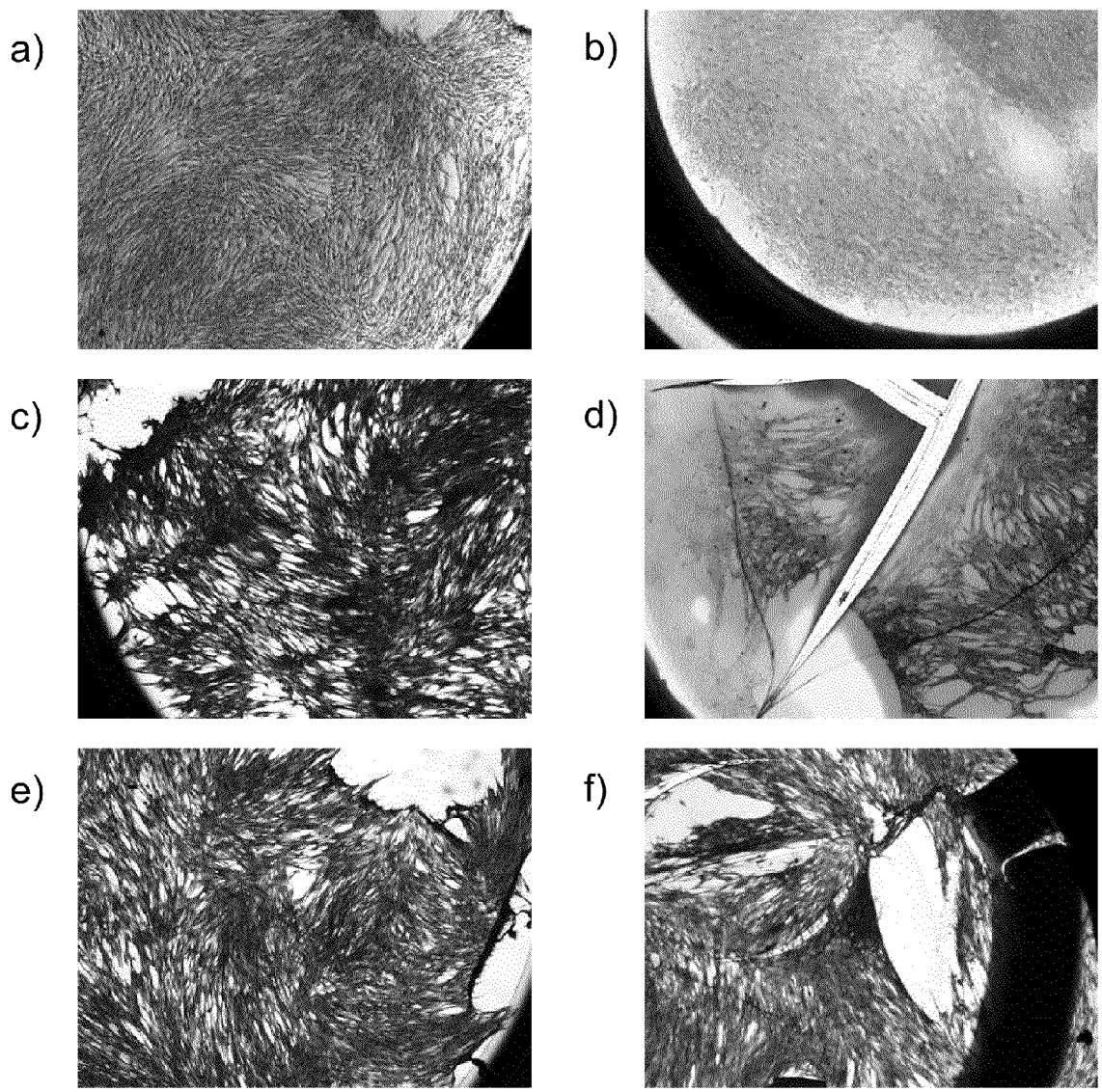
FIGS. 14A-F are microscopic images of coated surfaces after culture with MRC-5 cells and stained with crystal violet. The coatings were formed from monomers: TEGDA (*a*, *b*), GDMA (*c*, *d*), BDMA (*e*, *f*), using ethanol as a solvent (*a*, *c*, *e*) or DMF as a solvent (*b*, *d*, *f*).

All 96-well plates were sterilized by 25-35 kGy Gamma radiation prior to cell cytotoxicity analysis. Human lung fibroblasts (MRC5, ATCC# CCL-171) were grown to confluency in Iscove's Modified Dulbecco's Medium supplemented with 10% fetal bovine serum at standard cell culture conditions. Cells were harvested using 0.05% trypsin/EDTA and seeded at the density of 15,000 cells/well. Cells were grown at standard cell culture conditions (5% $CO_2$, 37° C.). The CellTiter 96® AQueous One Solution Cell Proliferation Assay (G3581, Promega Corporation) was used to determine the relative number of viable cells on each surface after 72 hours in culture. The assay was performed according to the manufacturer's protocol. Briefly, after aspiration of culture media, a 1:5 dilution of MTS tetrazolium reagent in phosphate buffered saline was added directly to cells. After 1 hour of incubation at 37° C. and 5% $CO_2$, the absorbance at 490 nm was recorded. CellBind® treated TOPAS surface was used as the uncoated substrate control. This data was used to determine (meth)acrylic formulation cytotoxicity as shown in FIG. 13. Surfaces with normalized absorbance of 80% or higher were considered as not toxic. Based on the results, all the tested surfaces were considered as non toxic. The tested surfaces were later stained with crystal violet and optical microscopy images were taken as shown in FIG. 14. The coatings were formed from monomers: TEGDA (a, b), GDMA (c, d), BDMA (e, f), using ethanol as a solvent (a, c, e) or DMF as a solvent (b, d, f). Crystal violet staining images showed that DMF solution polymerization lead to cracking for formulation GDMA and BDMA (see Table 6).

To prepare the less crosslinked swellable (meth)acrylate coatings, 100 µl of stock formulation SA02 as listed in Table 6 was dissolved in 9.9 ml of selected solvents as listed in Table 3 to obtain approximately 1% formulation solution. Due to miscibility issues, ethyl ether and hexane were not selected for this test. Then 1 µl of the solution was deposited into each well of a 96-well cyclic olefin plate. The plates were treated with vacuum plasma before formulation deposition. Specifically, the vacuum plasma treatment was Corning CellBind® treatment. Later the solvents were evaporated in nitrogen environment for 3 hr to remove the majority of the solvent and prevent condensation of humidity on the coating surface. Finally the plates were cured using Xenon RC-800 pulsed UV curing system for 60 seconds with dose of 10-15 mW/cm$^2$ in nitrogen environment to prevent oxygen inhibition of the free radical polymerization. As comparison, formulation SA02 was also dissolved to 1% in DMF for coating. 1 µl of the formulation was dispensed in each well. Then, the coating was exposed to Xenon RC-800 pulsed UV light at same dose without drying step to do solution polymerization. One replicate of the plates was stained with crystal violet. Crystal violet bound to the negative charged group in swellable (meth)acrylate to provide contrast under microscopy.

Figure 15:
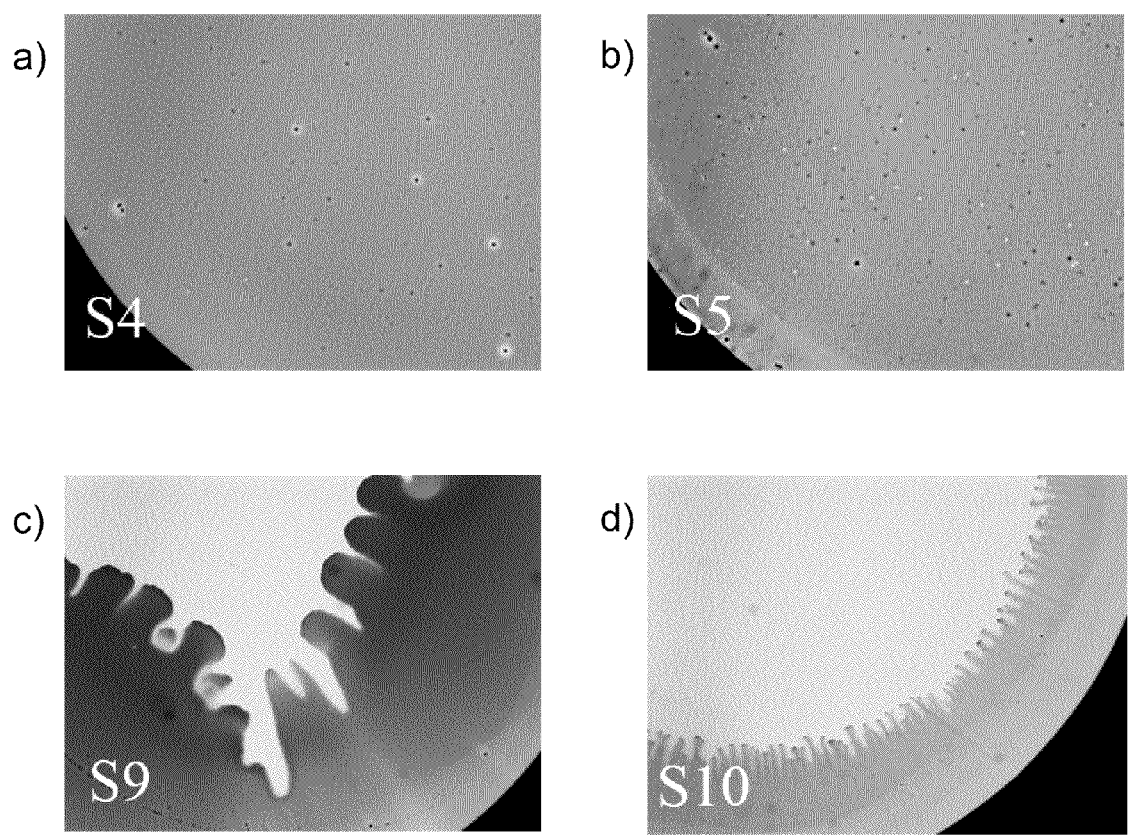
FIGS. 15A-D are microscopic images of crystal violet stained swellable (meth)acrylate layer in wells of a 96-well plate, using ethanol (*a*), 2-butanol (*b*), water (*c*), and DMF (*d*) as solvents in the process of preparing the swellable (meth) acrylate surface.

FIG. 15 shows microscopic images of crystal violet stained swellable (meth)acrylate layer in wells of a 96-well plate, using ethanol (a), 2-butanol (b), water (c), and DMF (d) as solvents in the process of preparing the swellable (meth)acrylate surface. Crystal violet staining showed that using acetone, methanol, ethyl acetate, ethanol, butanone, acetonitrile, 2-propanol, 2-butanol as solvent can provide uniform swellable (meth)acrylate coatings as shown by examples of ethanol and 2-butanol in FIG. 15. In contrast, water and DMF showed a large area of potential exposure of substrate. The coating from DMF solution polymerization showed no crystal violet staining which suggests either the coating failed or was washed out.

After polymerization peptide LysGlyGlyAsnGlyGlu-ProArgGlyAspThrTyrArgAlaTyr (SEQ ID NO: 1) was conjugated on the swellable (meth)acrylate coating surface (SA02) using EDC/NHS method. Briefly, 50 µL of 0.1 mM EDC and 0.05 mM NHS solution in DMF were dispensed in each well and allowed to react for 1.5 hr. Then, 50 µL of 1 mM peptide solution in 25 mM phosphate buffer pH 7.4 were dispensed into the well and allowed to react for 1.5 hr. Peptide solution was later replaced with 1M ethanolamine solution which was adjusted to pH 8.0-8.5. Finally the wells were washed with phosphate buffer and water.

To test stem cell culture, all experimental plates were sterilized prior to the cell seeding by spraying with 70% ETOH, drying in a laminar hood, and washing twice with 200 µl Dulbecco's Phosphate Buffered Saline (DPBS). H7 hES cells were seeded on peptide conjugated swellable (meth)acrylate surfaces at a density of 35,000 cells/well (96-well plate) in 100 µl of the chemically defined medium [(Xvivo10 from Lonza), 80 ng/ml basic fibroblast growth factor (bFGF), 0.5 ng/ml transforming growth factor-β1 (TGFβ1) from R&D Systems]. MATRIGEL™-coated wells were used as positive control for adhesion and growth of undifferentiated hES cells. Cells were cultured for 48 hrs under standard cell culture conditions (37° C. with 5% $CO_2$) and then were fixed and processed for AttoPhos assay to measure alkaline phosphatase activity, which is a known marker for undifferentiated hES cells.

AttoPhos assay was performed as follows: Briefly, at the end of incubation time, cells were rinsed with 150 µl of DPBS and fixed with 4% paraformaldehyde for 10 min at room temperature (70 µl/well of 96-well plate). The cells were washed once with 150 µl of DPBS, and treated for 10 min with 100 µl of AttoPhos fluorescent substrate for alkaline phosphatase (Promega) (diluted 1:3 in DPBS) protected from light. AttoPhos fluorescent intensity at 485/535 nm was obtained using Victor 3 microplate reader (Perkin Elmer). AttoPhos fluorescent intensity for experimental surfaces was expressed as % of fluorescent intensity of cells culture on MATRIGEL™ control.

Figure 16:
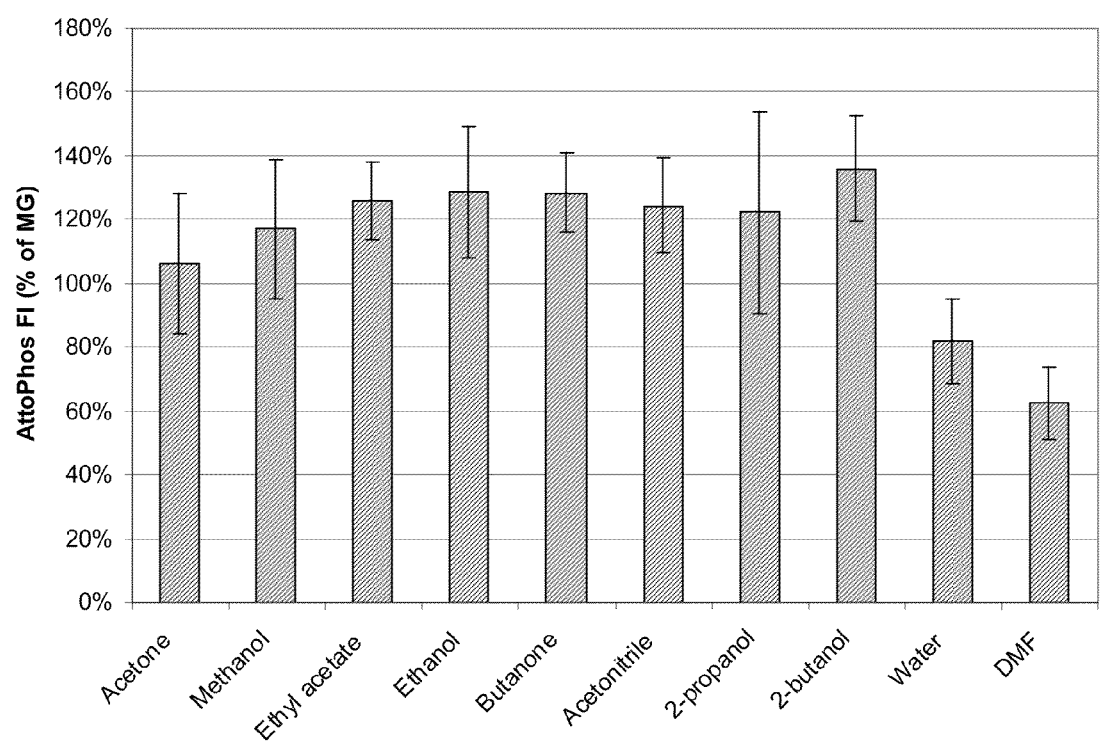
FIG. 16 is a bar graph showing AttoPhos fluorescence intensity of undifferentiated H7 hESC cultured for 48 hrs in chemically defined medium on a swellable (meth)acrylate substrate prepared with different solvents and conjugated with peptide LysGlyGlyAsnGlyGluProArgGlyAsp ThrTyr ArgAlaTyr (SEQ ID NO:1) (BSP peptide). The results were normalized against AttoPhos fluorescence intensity of hESC on MATRIGEL™ (MG) surface.

The AttoPhos results are shown in FIG. 16. The peptide conjugated swellable (meth)acrylate SA02 coatings processed with solvents: acetone, methanol, ethyl acetate, ethanol, butanone, acetonitrile, 2-propanol, 2-butanol, were similar or better than MATRIGEL™ in supporting undifferentiated stem cell culture. BCIP staining was performed to confirm normal undifferentiated stem cell colony morphology on these surfaces (data not shown). In contrast, coatings processed using water and DMF were less supportive for hESC culture.

Results and Discussion:

A broad range of solvents in addition to ethanol can be used in the bulk phase polymerization (in situ polymerization) process described. In embodiments, solvents providing good solubility to compositions in the formulations and solvents that are inert to the selected substrate provide good characteristics for polymerization. Low surface energy of solvents assists with the spreading of formulations. Low boiling point solvents can be completely or nearly completely removed before polymerization. As shown in the results described herein, solution polymerization can potentially lead to cracking of the coating for highly crosslinked coatings and may lead to uncoated patches on the substrate. Examples of suitable solvents for use with the methods described herein include, but are not limited to, acetone, methanol, ethyl acetate, ethanol, butanone, acetonitrile, 2-propanol, 2-butanol. Preferably the solvents used have boiling point ranging from about 34° C. to about 120° C., from about 50° C. to about 100° C., or about 70° C. to about 85° C. Ethanol and 2-propanol are good candidates for commercial production because of their solubility with the monomers, compatibility with plastic resins, low surface energy, hazardous waste management, and safety concerns.

Thus, embodiments of CELL CULTURE ARTICLE AND SCREENING are disclosed. One skilled in the art will appreciate that the arrays, compositions, kits and methods described herein can be practiced with embodiments other than those disclosed. The disclosed embodiments are presented for purposes of illustration and not limitation.

What is claimed is:

1. A method for producing a cell culture article having a synthetic polymer layer, comprising:
   (a) diluting one or more (meth)acrylate monomers in a solvent;
   (b) dispersing the diluted monomers on a surface of a cell culture substrate;
   (c) removing about 80% or more of the solvent; and
   (d) polymerizing the monomers on the surface of the cell culture substrate after removing the about 80% or more of the solvent to form the synthetic polymer layer attached to the surface of the cell culture substrate.

2. The method of claim 1, wherein removing the solvent comprises evaporating the solvent.

3. The method of claim 1, wherein the solvent has a boiling point of between about 50° C. and about 100° C.

4. The method of claim 1, wherein the solvent has a boiling point of between about 70° C. and about 85° C.

5. The method of claim 1, wherein the solvent is selected from the group consisting of acetone, methanol, ethyl acetate, ethanol, butanone, acetonitrile, 2-propanol, and 2-butanol.

6. The method of claim 1, wherein the solvent comprises ethanol or 2-propanol.

7. The method of claim 1, wherein the solvent comprises greater than 95% ethanol.

8. The method of claim 1, wherein the cell culture substrate is formed from a polymeric material.

9. The method of claim 1, wherein the cell culture substrate comprises a cyclic olefin copolymer.

10. The method of claim 9, further comprising plasma treating the surface of the cell culture substrate prior to dispersing the diluted monomers on the surface of the cell culture substrate.

11. The method of claim 1, wherein polymerizing the monomers comprises exposing the monomers to UV radiation.

12. The method of claim 11, wherein exposing the monomers to UV radiation comprises exposing the monomers to pulsed UV radiation.

13. The method of claim 12, wherein the pulsed UV radiation is delivered at a dose of between about 0.5 J/cm$^2$ and about 1.1 J/cm$^2$ at a power of between about 5 mW/cm$^2$ and about 100 mW/cm$^2$.

14. The method of claim 12, wherein exposing the monomers to pulsed UV radiation comprises exposing the monomers to radiation under nitrogen protection.

15. The method of claim 1, further comprising washing the synthetic polymer layer with a solution comprising the solvent.

16. The method of claim 1, wherein the one or more (meth)acrylate monomers are combinations of multi-functional and mono-functional (meth)acrylate monomers.

17. The method of claim 1, wherein polymerizing the monomers on the surface of the cell culture substrate to form the synthetic polymer layer comprises forming a swellable (meth)acrylate layer.

18. The method of claim 17, further comprising conjugating a polypeptide to the swellable (meth)acrylate layer.

19. The method of claim 1, wherein one or more (meth) acrylate monomers comprises glycerol dimethacrylate.

* * * * *